US012338472B2

(12) United States Patent
Cordero et al.

(10) Patent No.: US 12,338,472 B2
(45) Date of Patent: Jun. 24, 2025

(54) ISOLATION OF FUNGAL MELANIN AND USES IN EXTERNAL RADIATION SHIELDING AND HEAT CAPTURE

(71) Applicant: THE JOHNS HOPKINS UNIVERSITY, Baltimore, MD (US)

(72) Inventors: Radames J B Cordero, Baltimore, MD (US); Arturo Casadevall, Baltimore, MD (US); Raghav Vij, Pune (IN)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 924 days.

(21) Appl. No.: 17/415,694

(22) PCT Filed: Dec. 20, 2019

(86) PCT No.: PCT/US2019/068034
§ 371 (c)(1),
(2) Date: Jun. 17, 2021

(87) PCT Pub. No.: WO2020/132555
PCT Pub. Date: Jun. 25, 2020

(65) Prior Publication Data
US 2022/0042056 A1 Feb. 10, 2022

Related U.S. Application Data

(60) Provisional application No. 62/783,591, filed on Dec. 21, 2018, provisional application No. 62/898,948, filed on Sep. 11, 2019.

(51) Int. Cl.
*C12P 17/18* (2006.01)
*G21F 1/10* (2006.01)

(52) U.S. Cl.
CPC .............. *C12P 17/182* (2013.01); *G21F 1/10* (2013.01)

(58) Field of Classification Search
None
See application file for complete search history.

(56) References Cited

U.S. PATENT DOCUMENTS

| | | | |
|---|---|---|---|
| 5,047,447 A | 9/1991 | Gallas | |
| 5,380,359 A | 1/1995 | Honda et al. | |
| 5,538,752 A | 7/1996 | Blanchette et al. | |
| 7,354,150 B2 | 4/2008 | Sugimura et al. | |
| 8,586,090 B2 | 11/2013 | Dadachova et al. | |
| 9,450,043 B2 | 9/2016 | Nuzzo et al. | |
| 9,523,160 B2 | 12/2016 | Kim et al. | |
| 2005/0156496 A1 | 7/2005 | Takashima et al. | |
| 2007/0237829 A1* | 10/2007 | Dadachova | A61K 9/0019 977/774 |
| 2011/0281070 A1 | 11/2011 | Mittal et al. | |
| 2012/0132930 A1 | 5/2012 | Young et al. | |
| 2013/0056244 A1 | 3/2013 | Srinivas et al. | |
| 2014/0037674 A1 | 2/2014 | Dadachova et al. | |
| 2014/0257109 A1 | 9/2014 | Nishikubo | |
| 2016/0066601 A1 | 3/2016 | Herr et al. | |
| 2017/0066188 A1 | 3/2017 | Luo et al. | |
| 2019/0297880 A1 | 10/2019 | Shanmuganathan et al. | |

FOREIGN PATENT DOCUMENTS

| | | |
|---|---|---|
| CN | 103320332 | 9/2013 |
| EP | 3228192 | 10/2017 |
| RU | 2565178 | 10/2015 |
| WO | WO 2017/212500 | 12/2017 |
| WO | WO 2020/132555 | 6/2020 |

OTHER PUBLICATIONS

International Search Report and Written Opinion for PCT/US19/68034. Mailed Apr. 27, 2020. 11 pages.
Albuquerque et al., Quorum sensing-mediated, cell density-dependent regulation of growth and virulence in Cryptococcus neoformans., MBio., (2013), vol. 5(1):e00986-00913. 15 pages.
Al-Doory., The ultrastructure of Cryptococcus neoformans., Sabouraudia: Journal of Medical and Veterinary Mycology., (1971), pp. 115-118, vol. 9(2).
Almagro Armenteros et al., SignalP 5.0 improves signal peptide predictions using deep neural networks., Nature Biotechnology., (2019), pp. 420-423, vol. 37.
Alviano et al., Characterization of Fonsecaea pedrosoi melanin., Journal of Genetic Microbiology., (1991), pp. 837-844, vol. 137.
Baker et al., Chitinases are essential for sexual development but not vegetative growth in Cryptococcus neoformans. Eukaryot Cell., (2009), pp. 1692-1705, vol. 8(11).
Baker et al., Chitosan, the deacetylated form of chitin, is necessary for cell wall integrity in Cryptococcus neoformans., Eukaryotic Cell., (2007), pp. 855-867, vol. 6(5).
Banks et al., A chitin synthase and its regulator protein are critical for chitosan production and growth of the fungal pathogen Cryptococcus neoformans., Eukaryotic Cell., (2005), pp. 1902-1912, vol. 4(11).
Bissig et al., PMEL Amyloid Fibril Formation: The Bright Steps of Pigmentation., International Journal of Molecular Sciences., (2016), vol. 17(9):1438. 14 pages.
Brach et al., Reassessment of the role of plasma membrane domains in the regulation of vesicular traffic in yeast., Journal of Cell Science., (2011), pp. 328-337, vol. 124(3).
Bull., Chemical composition of wild-type and mutant Aspergillus nidulans cell walls. The nature of polysaccharide and melanin constituents., Journal of Genetic Microbiology., (1970), pp. 75-94, vol. 63.

(Continued)

*Primary Examiner* — Christian L Fronda
(74) *Attorney, Agent, or Firm* — Lisa Mueller; Casimir Jones SC

(57) ABSTRACT

Described are methods including cell wall-associated melanin extraction and extracting melanin from microbes producing extracellular vesicles comprising melanin. Further described are composition comprising melanin, melanin coated articles and methods of coating an article. Uses of melanin in methods of heat generation and microwave radiation protection are also described.

10 Claims, 20 Drawing Sheets

(56) References Cited

OTHER PUBLICATIONS

Bungeler et al., Insight into the Final Step of the Supramolecular Buildup of Eumelanin., Langmuir., (2017), pp. 6895-6901, vol. 33.
Bungeler et al., The Supramolecular Buildup of Eumelanin: Structures, Mechanisms, Controllability., International Journal of Molecular Sciences., (2017), vol. 18(9):1901. 14 pages.
Cadieux et al., The Mannoprotein Cig1 supports iron acquisition from heme and virulence in the pathogenic fungus Cryptococcus neoformans., Journal of Infectious Diseases., (2013), pp. 1339-1347, vol. 207(8).
Camacho et al., N-acetylglucosamine affects Cryptococcus neoformans cell-wall composition and melanin architecture., Microbiology., (2017), pp. 1540-1556, vol. 163.
Cao et al., Selenomelanin: An abiotic selenium analogue of pheomelanin. J.Am. Chem. Soc. (2020), 142, 12802-12810.
Casadevall et al., Fungal melanins differ in planar stacking distances., PLoS One., (2012), vol. 7:e30299. 6 pages.
Chaskes et al., Pigment production by Cryptococcus neoformans from para- and ortho-Diphenols: effect of the nitrogen source., Journal of Clinical Microbiology., (1975), pp. 509-514, vol. 1(6).
Chatterjee et al., Demonstration of a common indole-based aromatic core in natural and synthetic eumelanins by solid-state NMR., Organic and Biomolecular Chemistry., (2014), pp. 6730-6736, vol. 12.
Chatterjee et al., Solid-state NMR Reveals the Carbon-based Molecular Architecture of Cryptococcus neoformans Fungal Eumelanins in the Cell Wall., J Biol Chem., (2015), pp. 13779-13790, vol. 290(22).
Chatterjee et al., The melanization road more traveled by: precursor substrate effects on melanin synthesis in cell-free and fungal cell systems., Journal of Biological Chemistry., (2018), p. 20157-20168, vol. 293(52).
Chatterjee et al., Using solid-state NMR to monitor the molecular consequences of Cryptococcus neoformans melanization with different catecholamine precursors., Biochemistry., (2012), pp. 6080-6088, vol. 51(31).
Chi et al., Proteomic and bioinformatic characterization of the biogenesis and function of melanosomes. Journal of Proteome Research., (2006), pp. 3135-3144, vol. 5(11).
Christensen et al., Melanization immune responses in mosquito vectors., Trends Parasitol., (2005), pp. 192-199, vol. 21(4).
Chun et al., A major role for capsule-independent phagocytosis-inhibitory mechanisms in mammalian infection by Cryptococcus neoformans., Cell Host & Microbe., (2011), pp. 243-251, vol. 9(3).
Clancy et al., Ultrastructural organization of eumelanin from Sepia officinalis measured by atomic force microscopy., Biochemistry., (2001), pp. 13353-13360, vol. 40(44).
Clarke et al., Integrated Activity and Genetic Profiling of Secreted Peptidases in Cryptococcus neoformans Reveals an Aspartyl Peptidase Required for Low pH Survival and Virulence., PLoS Pathogens., (2016), vol. 12:e1006051. 30 pages.
Cordero et al., Functions of fungal melanin beyond virulence., Fungal Biology Reviews., (2017), pp. 99-112, vol. 31(2).
Cordero et al., Impact of Yeast Pigmentation on Heat Capture and Latitudinal Distribution., Current Biology., (2018), pp. 2657-2664, vol. 28(16).
Cordero et al., Microbial melanins for radioprotection and bioremediation. Microbial Biotechnology. (2017), 10(5), 1186-1190.
Cordero., Melanin for space travel radioprotection., Environmental Microbiology., (2017), pp. 2529-2532, vol. 19(7).
Dadachova et al., The radioprotective properties of fungal melanin are a function of its chemical composition, stable radical presence and spatial arrangement. Pigment Cell Melanoma Res. (2007), 21;192-199.
Dange et al., Blm10 protein promotes proteasomal substrate turnover by an active gating mechanism., Journal Biological Chemistry., (2011), pp. 42830-42839, vol. 286(50).
D'Ischia et al., Chemical and structural diversity in eumelanins: unexplored bio-optoelectronic materials., Angewandte Chemie International Edition England., (2009), pp. 3914-3921, vol. 48(22).
D'Ischia et al., Melanins and melanogenesis: methods, standards, protocols., Pigment Cell Melanoma Research., (2013), pp. 616-633, vol. 26.
D'Souza et al., Cyclic AMP-dependent protein kinase controls virulence of the fungal pathogen Cryptococcus neoformans., Molecular Cell Biology., (2001), pp. 3179-3191, vol. 21(9).
Eisenman et al., Microstructure of cell wall-associated melanin in the human pathogenic fungus Cryptococcus neoformans., Biochemistry., (2005), pp. 3683-3693, vol. 44(10).
Eisenman et al., Synthesis and assembly of fungal melanin., Applied Microbiology and Biotechnology., (2012), pp. 931-940, vol. 93.
Eisenman et al., Vesicle-associated melanization in Cryptococcus neoformans., Microbiology., (2009), pp. 3860-3867, vol. 155.
Fankhauser et al., Identification of GPI anchor attachment signals by a Kohonen self-organizing map., Bioinformatics., (2005), pp. 1846-1852, vol. 21(9).
Foderaro et al., MCC/Eisosomes Regulate Cell Wall Synthesis and Stress Responses in Fungi., Journal of Fungi (Basel)., (2017), vol. 3(4):61. 18 pages.
Franzen et al., Morphometric and densitometric study of the biogenesis of electron-dense granules in Fonsecaea pedrosoi., FEMS Microbiology Letters., (1999), pp. 395-402, vol. 173(2).
Franzen et al., Ultrastructural characterization of melanosomes of the human pathogenic fungus Fonsecaea pedrosoi., Journal of Structural Biology., (2008), pp. 75-84, vol. 162(1).
Gaigg et al., Synthesis of sphingolipids with very long chain fatty acids but not ergosterol is required for routing of newly synthesized plasma membrane ATPase to the cell surface of yeast., Journal of Biological Chemistry., (2005), pp. 22515-22522, vol. 280(23).
Garcia-Rivera et al., Comparative analysis of Cryptococcus neoformans acid-resistant particles generated from pigmented cells grown in different laccase substrates., Fungal Genetics and Biology., (2005), pp. 989-999, vol. 42(12).
Geddes et al., Secretome profiling of Cryptococcus neoformans reveals regulation of a subset of virulence-associated proteins and potential biomarkers by protein kinase A., BMC Microbiology., (2015), vol. 15:206.
Gomez et al., Melanin and fungi. Current Opinion on Infectious Diseases., (2003), pp. 91-96, vol. 16.
Grossman et al., Membrane potential governs lateral segregation of plasma membrane proteins and lipids in yeast., Embo J., (2007), pp. 1-8, vol. 26(1).
Groux-Degroote et al., Glycolipid-dependent sorting of melanosomal from lysosomal membrane proteins by lumenal determinants., Traffic., (2008), pp. 951-963, vol. 9.
Gueymard et al., Proposed reference irradiance spectra for solar energy systems testing. Solar Energy. (2002) vol. 73, No. 6, pp. 443-467.
Hegnauer et al., Ultrastructure of native and synthetic Agaricus bisporus melanins. Implications as to the compartmentation of melanogenesis in fungi., Experimental Mycology., (1985), pp. 221-229, vol. 9(3).
Hill., The function of melanin or six blind people examine an elephant., Bioessays., (1992), pp. 49-56, vol. 14.
Homer et al., Intracellular Action of a Secreted Peptide Required for Fungal Virulence., Cell Host & Microbe., (2016), pp. 849-864, vol. 19(6).
Hommel et al., Titan cells formation in Cryptococcus neoformans is finely tuned by environmental conditions and modulated by positive and negative genetic regulators., PLoS Pathogens., (2018), vol. 14:e1006982. 38 pages.
Hong et al., Progressive fuzzy cation-pi assembly of biological catecholamines., Sci Adv., (2018), vol. 4(9):eaat7457. 11 pages.
Hu et al., Transcriptional regulation by protein kinase A in Cryptococcus neoformans., PLoS Pathogens., (2007), vol. 3:e42. 18 pages.
Huffnagle et al., Down-regulation of the afferent phase of T cell-mediated pulmonary inflammation and immunity by a high melanin-producing strain of Cryptococcus neoformans., Journal of Immunology., (1995), pp. 3507-3516, vol. 155.
Ito., The IFPCS presidential lecture: a chemist's view of melanogenesis., Pigment Cell Research., (2003), pp. 230-236, vol. 16.

(56) References Cited

OTHER PUBLICATIONS

Jung et al., (2009) Role of ferroxidases in iron uptake and virulence of Cryptococcus neoformans., Eukaryotic Cell., (2009), pp. 1511-1520, vol. 8.

Kwon-Chung et al., Utilization of indole compounds by Cryptococcus neoformans to produce a melanin-like pigment. Journal of Clinical Microbiology., (1983), pp. 1419-1421, vol. 18(6).

Liu et al., Isolation and biophysical studies of natural eumelanins: applications of imaging technologies and ultrafast spectroscopy., Pigment Cell Research., (2003), pp. 606-618, vol. 16.

Liu et al., Systematic genetic analysis of virulence in the human fungal pathogen Cryptococcus neoformans., Cell., (2008), pp. 174-188, vol. 135(1).

Łopusiewicz., The isolation, purification and analysis of the melanin pigment extracted from Armillaria mellea rhizomorphs., World Scientific News., (2018), pp. 135-153, vol. 100.

Ludvigsen et al., Three-dimensional structure in solution of barwin, a protein from barley seed. Biochemistry., (1992), pp. 8783-8789, vol. 31.

Martinez et al., Susceptibility of Cryptococcus neoformans biofilms to antifungal agents in vitro., Antimicrobial Agents and Chemotherapy., (2006), pp. 1021-1033, vol. 50(3).

Meredith et al., Radiative relaxation quantum yields for synthetic eumelanin. Photochemistry and Photobiology, (2004), 79(2): 211-216.

Meredith et al., The physical and chemical properties of eumelanin., Pigment Cell Research., (2006), pp. 572-594, vol. 19(6).

Momen-Heravi et al., Current methods for the isolation of extracellular vesicles., Biological Chemistry., (2013), pp. 1253-1262, vol. 394(10).

Mulholland et al., Ultrastructure of the yeast actin cytoskeleton and its association with the plasma membrane., Journal of Cellular Biology., (1994), pp. 381-391, vol. 125(2).

Nosanchuk et al., Budding of melanized Cryptococcus neoformans in the presence or absence of L-dopa., Microbiology., (2003), pp. 1945-1951, vol. 149.

Nosanchuk et al., Cellular charge of Cryptococcus neoformans: contributions from the capsular polysaccharide, melanin, and monoclonal antibody binding., Infectious Immunology., (1997), pp. 1836-1841, vol. 65(5).

Nosanchuk et al., Impact of melanin on microbial virulence and clinical resistance to antimicrobial compounds., Antimicrobial Agents and Chemotherapy., (2006), pp. 3519-3528, vol. 50(11).

Nosanchuk et al., The contribution of melanin to microbial pathogenesis., Cell Microbiology., (2003), pp. 203-223, vol. 5.

Oliveira et al., Cryptococcus neoformans cryoultramicrotomy and vesicle fractionation reveals an intimate association between membrane lipids and glucuronoxylomannan., Fungal Genetics & Biology., (2009), pp. 956-963, vol. 46(12).

O'Meara et al., Interaction of Cryptococcus neoformans Rim101 and protein kinase A regulates capsule., PLoS Pathogens., (2010), vol. 6(2):e1000776.

Pacelli et al., Melanin is effective in protecting fast and slow growing fungi from various types of ionizing radiation. Environmental Microbiology (2017) 19(4), 1612-1624.

Panepinto et al., The cell biology of virulence—lessons from the pathogenic fungus Cryptococcus neoformans., Communicating Current Research and Educational Topics and Trends in Applied Microbiology., (2007), A. Méndez-Vilas (Ed.) Formatex. 10 pages.

Panzella et al., The Late Stages of Melanogenesis: Exploring the Chemical Facets and the Application Opportunities. Int J Mol Sci., (2018), vol. 19(6):1753. 16 pages.

Perez-Dulzaides et al., Cell-wall dyes interfere with cryptococcus neoformans melanin deposition. Microbiology (2018) 164:1012-1022.

Pombeiro-Sponchiado et al., Production of Melanin Pigment by Fungi and it's Biotechnological Applications. Melanin. 2017. 47-75.

Prados-Rosales et al., Structural Characterization of Melanin Pigments from Commercial Preparations of the Edible Mushroom *Auricularia auricula.*, Journal of Agricultural Food Chemistry., (2015) pp. 7326-7332, vol. 63(33).

Prota., Progress in the chemistry of melanins and related metabolites., Medicinal Research Reviews., (1988), pp. 525-556, vol. 8(4).

Riesz et al., Quantitative scattering of melanin solutions., Biophysical Journal., (2006), pp. 4137-4144, vol. 90(11).

Rodrigues et al., Extracellular vesicles produced by Cryptococcus neoformans contain protein components associated with virulence., Eukaryotic Cell., (2008), pp. 58-67, vol. 7(1).

Rodrigues et al., Vesicular mechanisms of traffic of fungal molecules to the extracellular space., Current Opinion in Microbiology., (2013), pp. 414-420, vol. 16(4).

Rodrigues et al., Vesicular polysaccharide export in Cryptococcus neoformans is a eukaryotic solution to the problem of fungal trans-cell wall transport., Eukaryotic Cell., (2007), pp. 48-59, vol. 6(1).

San-Blas et al., Cladosporium carrionii and Hormoconis resinae (C. resinae): cell wall and melanin studies., Current Microbiology., (1996), pp. 11-16, vol. 32.

Sarna et al., Identification and characterization of melanin in tissues and body fluids., Folia Histochemica Cytochemica., (1978), pp. 275-286, vol. 16(4).

Sealy et al., Eumelanins and pheomelanins: characterization by electron spin resonance spectroscopy., Science., (1982), pp. 545-547, vol. 217(4559).

Seiji et al., Chemical composition and terminology of specialized organelles (melanosomes and melanin granules) in mammalian melanocytes., Nature., (1963), pp. 1082-1084, vol. 197.

Solano., Melanin and Melanin-related polymers as materials with biomedical and biotechnological applications—cuttlefish ink and mussel foot proteins as inspired biomolecules., International Journal of Molecular Sciences., (2017), vol. 18(7): 1561. 18 pages.

Steenbergen et al., Cryptococcus neoformans interactions with amoebae suggest an explanation for its virulence and intracellular pathogenic strategy in macrophages., Proc Natl Acad Sci U S A., (2001), pp. 15245-15250, vol. 98(26).

Stoetzner et al., The morphology of Cryptococcus neoformans in human cryptococcosis. A light-,phase-contrast and electron-microscopic study., Mycopathol et Mycologica Applicata., (1971), pp. 327-335, vol. 45.

Tajima et al., Solubilized melanin suppresses macrophage function., FEBS Open Bio., (2019), pp. 791-800, vol. 9(4).

Tsirilakis et al., Methylxanthine inhibit fungal chitinases and exhibit antifungal activity., Mycopathologia., (2012), pp. 83-91, vol. 173.

Upadhyay et al., Subcellular Compartmentalization and Trafficking of the Biosynthetic Machinery for Fungal Melanin., Cell Rep., (2016), pp. 2511-2518, vol. 14(11).

Walker et al., Melanin externalization in Candida albicans depends on cell wall chitin structures., Eukaryotic Cell., (2010), pp. 1329-1342, vol. 9(9).

Walker et al., The Viscoelastic Properties of the Fungal Cell Wall Allow Traffic of AmBisome as Intact Liposome Vesicles., MBio., (2018), vol. 9(1):e02383-17. 15 pages.

Walton et al., Novel gene functions required for melanization of the human pathogen Cryptococcus neoformans., Molecular Microbiology., (2005), pp. 1381-1396, vol. 57(5).

Wang et al., Cryptococcus neoformans melanin and virulence: mechanism of action., Infection and Immunity., (1995), pp. 3131-3136, vol. 63(8).

Wang et al., Growth of Cryptococcus neoformans in presence of L-dopa decreases its susceptibility to amphotericin B., Antimicrob Agents Chemother., (1994), pp. 2648-2650, vol. 38(11).

Wang et al., Melanin, melanin "ghosts," and melanin composition in Cryptococcus neoformans. Infect Immun., (1996), pp. 2420-2424, vol. 64(7).

Wang et al., WdChs4p, a homolog of chitin synthase 3 in *Saccharomyces cerevisiae*, alone cannot support growth of Wangiella (Exophiala) dermatitidis at the temperature of infection., Infection and Immunity., (1999), pp. 6619-6630, vol. 67(12).

Watt et al., The supramolecular structure of melanin. Soft Matter, (2009), 5, 3754-3760.

White., Melanin: a naturally occurring cation exchange material., Nature., (1958), pp. 1427-1428, vol. 182.

(56) References Cited

OTHER PUBLICATIONS

Wikipedia.com Hydrochloric Acid. Dec. 19, 2018. Retrieved from the internet Jun. 15, 2022. 10 pages.
Wolf et al., Interaction of Cryptococcus neoformans extracellular vesicles with the cell wall., Eukaryotic Cell., (2014), pp. 1484-1493, vol. 13(12).
Xiao et al., Elucidation of the hierarchical structure of natural eumelanins., J R Soc Interface., (2018), vol. 15(140) 10 pages.
Zajac et al., The fundamental unit of synthetic melanin: a verification by tunneling microscopy of X-ray scattering results., Biochim Biophys Acta., (1994), pp. 271-278, vol. 1199(3).
Zhang et al., Cryptococcal phosphoglucose isomerase is required for virulence factor production, cell wall integrity and stress resistance. FEMS Yease Research, (2015), 15, fov072. 9 pages.
Zhong et al., Following fungal melanin biosynthesis with solid-state NMR: biopolymer molecular structures and possible connections to cell-wall polysaccharides., Biochemistry., (2008), pp. 4701-4710, vol. 47(16).
Zhu et al., Laccase of Cryptococcus neoformans is a cell wall-associated virulence factor., Infection and Immunity., (2001), pp. 5589-5596, vol. 69(9).
European Patent Office, Extended European Search Report for EP Application No. 19901392.1 mailed Jan. 11, 2023.
International Search Report and Written Opinion for PCT/US19/68043. Mailed Mar. 24, 2020. 9 pages.
Lopusiewicz et al., New Poly(lactic acid) Active Packaging Composite Films Incorporated with Fungal Melanin., Polymers., 2018, vol. 10(4):386. 22 pages.
Malo et al., Morphological changes in melanized and non-melanized Cryptococcus neoformans cells post exposure to sparsely and densely ionizing radiation demonstrate protective effect of melanin. Fungal Biol. Jun. 2018;122(6):449-456.
MatterHackers. How to succeed when 3d printing with hylon. MatterHackers. www.matterhackers.com/articles/printing-with-nylon . 2014. Retrieved from the internet Feb. 25, 2020. 2 pages.
Nambier et al., Polymer-composite materials for radiation protection. ACS Appl Mater Interfaces. Nov. 2012;4(11):5717-26.
Nasa Science, Plastic Spaceships | Science Mission Directorate [Online]. P.L.B. 2005. Available at: https://science.nasa.gov/science-news/science-at-nasa/2005/25aug_plasticspaceships [Accessed: Mar. 13, 2017]. Printed May 16, 2022. 10 pages.
Ngo et al., Additive manufacturing (3D printing): A review of materials, methods, applications and challenges., Composites Part B: Engineering., 2018, vol. 143. pp. 172-196.
Ou-Yang et al., Spectral responses of melanin to ultraviolet A irradiation. J Invest Dermatol. Feb. 2004;122(2):492-6.
Shin et al., Melanin Nanoparticle-Incorporated Silk Fibroin Hydrogels for the Enhancement of Printing Resolution in 3D-Projection Stereolithography of Poly(ethylene glycol)-Tetraacrylate Bio-ink. ACS Appl Mater Interfaces. Jul. 18, 2018;10(28):23573-23582.
Shunk et al., A self-replicating radiation shield for human deep space exploration: radiotrophic fungi can attenuate ionizing radiation aboard the international space station. bioRxiv. 2020. 16 pages.
Viskadourakis et al., Electromagnetic shielding effectiveness of 3D printed polymer composites., Applied Physics A Solids and Surfaces., 2017, vol. 123(12):736. 7 pages.
Wang et al., Mechanical properties of thermoplastic elastomers of poly(butylene terephthalate) and poly(ethylene glycol) in a bending deformation., Journal of Applied Polymer Science., 1994, vol. 51. pp. 145-151.

\* cited by examiner

ISOLATION OF FUNGAL MELANIN AND USES IN EXTERNAL RADIATION SHIELDING AND HEAT CAPTURE

CROSS-REFERENCE TO RELATED APPLICATIONS

This claims priority to U.S. Provisional Patent Application No. 62/783,591, filed on Dec. 21, 2018, and U.S. Provisional Patent Application No. 62/898,948, filed on Sep. 11, 2019, the entire contents of each of which are fully incorporated herein by reference.

STATEMENT OF GOVERNMENTAL INTEREST

This invention was made with government support under grant no. R01AI052733 awarded by the National Institutes of Health. The government has certain rights in the invention.

TECHNICAL FIELD

This present disclosure related to methods of isolating fungal melanin and compositions, coated articles, and methods of use thereof.

BACKGROUND OF THE INVENTION

Melanins are exceptional biopolymers capable of interacting and/or absorbing all forms of electromagnetic radiation. This optical capacity derives from their complex molecular organization, including graphite-like structures of phenolic/indolic polymers that form spherical nanoparticles and larger structures thereof. The capacity of melanins to interact with radiation makes them good radiation shielding materials. Most of the absorbed radiation energy by melanin is effectively translated into heat; a property that could be exploited in solar thermal energy systems. In addition, melanin biopolymers are attractive for multiple biotech and biomedical applications including bioelectronics, radioprotection, optics, cosmetics, printing, and drug delivery.

Melanins are present in animals, plants, fungi, and bacteria. Fungi are the richest source, capable of synthesizing melanins from at least three different biosynthetic pathways, utilizing 1,8-dihydroxynapthalene (DHN), tyrosine, or tyrosine derivatives like dihydroxyphenylalanine (DOPA).

Multiple fungal species produce melanin constitutively (e.g., *Aureobasidium melanogenum*, *Exophiala dermititidis*) and others require the provision of a melanin precursor (e.g., *Gliocephalotrichum simplex*, *Cryptococcus neoformans*). For example, *G. simplex* is a filamentous fungus that secretes a tyrosinase enzyme and, when grown in media supplemented with L-Tyrosine, it produces significant amounts of extracellular melanin nanoparticles. Similarly, *C. neoformans* is a perfectly spherical yeast of 2-15 nm in diameter that can produce a melanin coat surrounding its cell wall via the oxidation of exogenous phenolic compounds (e.g., dopamine, DOPA, epinephrine, methyl-DOPA) by a laccase enzyme. This melanin coat is formed by a connected network of melanin nanoparticles of 30-60 nm in diameter. Simple and cost-effective melanin extraction methods are needed to produce melanin in large quantities inexpensively so the compound may be used in many commercial applications. Melanotic fungi present rich melanin sources for industrial applications.

SUMMARY OF THE INVENTION

Disclosed herein are methods of purifying cell wall-associated melanin comprising the steps of heating a melanin producing microbe in 6N hydrochloric acid, and extracting the melanin using a chloroform:methanol:saline mixture.

Disclosed herein are methods of purifying extracellular melanin nanoparticles comprising the steps of: providing a culture of microbes producing extracellular vesicles comprising melanin; removing the microbes from the culture forming a cell free supernatant comprising extracellular vesicles comprising melanin; sedimenting the extracellular vesicles comprising melanin; and collecting the extracellular vesicles comprising melanin.

Also disclosed herein are compositions comprising melanin, melanin coated articles and methods of producing a melanin coated article comprising the steps of: applying a composition comprising melanin to the surface of an article; and drying the composition.

Further disclosed herein are methods of heating an article comprising providing a melanin coated article and exposing the article to light, whereby the temperature of the article is increased.

Other aspects of the invention will become apparent by consideration of the detailed description and accompanying drawings.

BRIEF DESCRIPTION OF THE DRAWINGS

FIG. 1A is an image of an example of L-DOPA melanized *Cryptococcus* liquid culture. FIG. 1B is a light microscopy negative-stained (India ink) image of a *Cryptococcus* yeast cell with a melanized cell wall (inner black circle) surrounded by a polysaccharide capsule (outer white layer) that excludes the ink particles in background. Scale bar, 10 µm. FIG. 1C is an image of isolated *Cryptococcus* melanin using the extraction methods of the present invention. Scale bar, 10 µm. FIG. 1D is a scanning electron microscopy image revealing rounded hollow micron sized particles. FIG. 1E is an image of one gram of dried *Cryptococcus* melanin exhibiting a dark/opaque appearance due to its high light absorbance. FIG. 1F shows that melanin microshells exhibit a broad-band monotonic absorption spectrum, which is typical of melanins covering the whole solar irradiance range.

FIG. 2A is transmission electron micrographs of extracellular melanin nanoparticles isolated by ultracentrifugation from culture supernatants. Scale bar, 100, 10 and 1 µm (left to right). FIG. 2B is a graph of the dynamic light scattering (DLS) measurements of extracellular melanin granules revealing a dominant monodisperse population with a hydrodynamic diameter of approximately 50 nm. FIG. 2C is the monotonic broad-band optical absorption spectra of the extracellular melanin granules, which is typical of melanin. FIG. 2D is an image of purification of extracellular melanin granules using differential density ultracentrifugation. Percoll density gradients of extracellular melanin granules (right tube) relative to density bead standards (left tube).

FIG. 3A is an image of concentrated melanized yeast cells poured and air dried on a plastic surface forming a thick biofilm coat. FIG. 3B is the broad-band optical absorption spectra (300-1500 nm) of the melanin biofilm covering the entire solar irradiance (adapted from Cordero, R. J. B., et al. 2018. *Current Biology*).

FIG. 6D shows images and graphs of coating aluminum foil with a fungal melanized biofilm dampening heating following 30 second irradiation inside a microwave oven. Bars graphs represent mean apparent temperature±min/max counts. The thermal shielding capacity of melanized yeast cells (FIG. 6E) and isolated melanin (FIG. 6F) was confirmed using a directed radiated source (Biotage® Initiator).

FIG. 9A is a visible image of 50 mg of melanin samples loaded in a 48-well microtiter plate. FIG. 9B shows the infrared images of samples before and after 12-minute irradiation and a graph of the mean temperature values. Error bars depict maximum and minimum temperature values.

DETAILED DESCRIPTION OF THE INVENTION

Figure 1A:
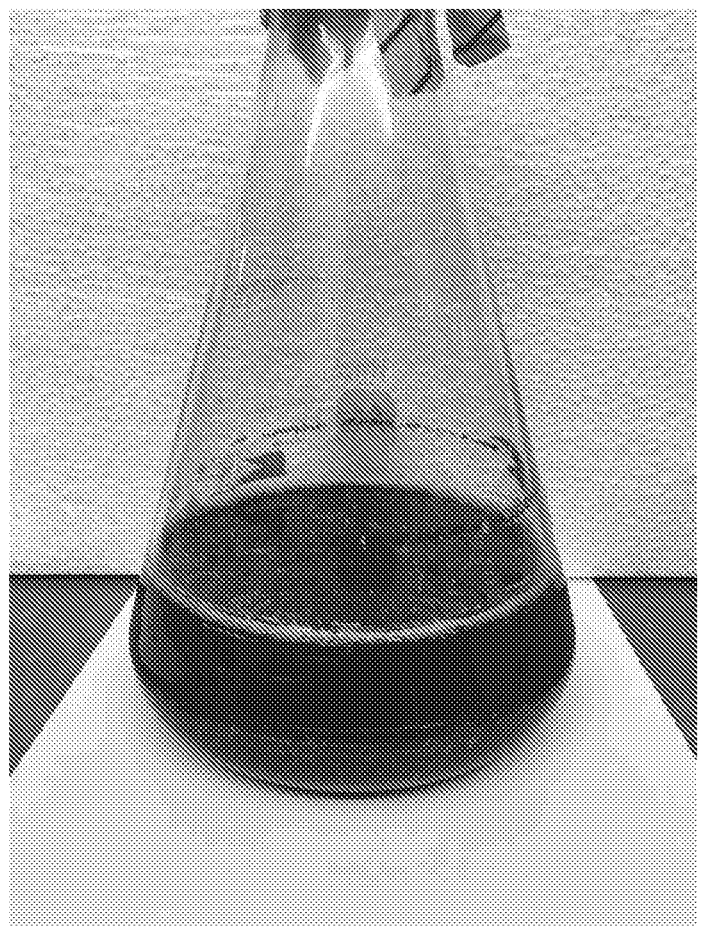
FIGS. 1A-1F illustrate microscopic characteristics of cell wall-associated melanin from *C. neoformans*.
Figure 1B:
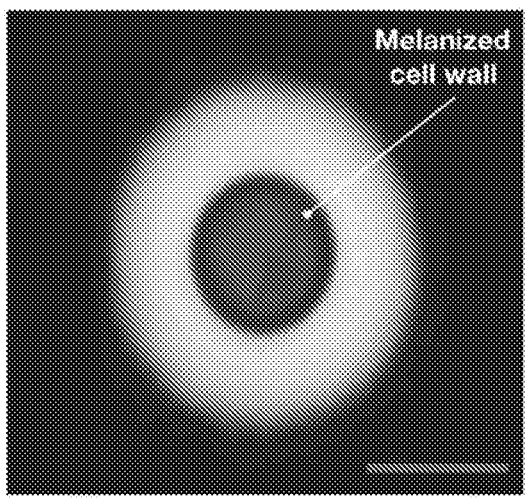

One of the embodiments of the present invention are two methods for extracting fungal melanins (1) associated with the cell wall (also referred to herein as cell well-associated melanins) and (2) secreted to the extracellular environment. The cell wall-associated melanin extraction method comprises the steps of heating a melanin producing microbe in 6N HCl; and extracting the melanin using a chloroform:methanol:saline mixture. The cell wall-associate melanin, or microshells, may be lyophilized or dried and then placed on a surface. Alternatively, the cell wall-associated melanin may be directed placed on a surface. In the methods of the present invention, it is preferred that the heating steps comes before the extracting step. Suitable temperatures used during the heating step are in the range of 60° C. to 120° C. A suitable duration of the heating step is in the range of 30 minutes to 24 hours. A suitable mixture has a concentration in the range of 8 parts chloroform:4 parts methanol:3 parts saline. Alternatively, a suitable mixture may have a concentration in the range of 7-10 parts chloroform:3-5 parts methanol:1-5 parts saline.

Another embodiment of the present invention is a method of extracellular melanin isolation that relies on the ability of microbial extracellular vesicles to melanize. The method comprises the steps of providing a culture of microbes producing extracellular vesicles containing melanin, removing the microbes from the culture forming a cell free supernatant comprising extracellular vesicles containing melanin, sedimenting the extracellular vesicles containing melanin, and collecting the extracellular vesicles containing melanin. The extracellular vesicles of the present invention may comprise cellular enzymes that produce melanin extracellularly so melanin is produced within the vesicle while outside the cell. The extracellular vesicles producing melanin may be lyophilized or dried and then placed on a surface. Alternatively, the extracellular vesicles producing melanin may be directly placed on a surface.

Another embodiment of the present invention is drying a culture of melanin producing microbes and using them to coat surfaces. The melanin-producing microbial cells may be concentrated by sedimentation and dried by lyophilizing forming thin flakes (or bioflakes), as examples. The melanin-producing microbes may be dried before or after being applied to a surface.

Another embodiment of the present invention is a method of producing a melanin coated article and a melanin coated article. The method comprises the steps of applying a composition comprising melanin producing microbes, cell wall-associated melanin, extracellular vesicles comprising melanin, or a combination thereof to a surface; and drying the composition. The drying step may come before or after the step of applying the composition to a surface. An example of a suitable adherent is a polymer. Examples of suitable microbes used in the present invention are *Cryptococcus neoformans, Aureobasidium melanogenum, Wangiella dermititidis, Cryomyces antarcticus, Cryptococcus neoformans* modified cell wall mutants thereof (*C. neoformans* cap59, *C. neoformans* chs3, *C. neoformans* csr2), *Exophiala dermititidis, Agaricus biscporus, Cladosporium sphaerospermum,* and combinations thereof. Examples of suitable surfaces of the article used in the present invention include plastic, glass, metal, wood, ceramic, aluminum, fibers, and polystyrene.

Another embodiment of the present invention is a method of generating heat or a method of heating an article. The method comprises the steps of applying a composition comprising melanin producing microbes, cell wall-associated melanin, extracellular vesicles comprising melanin, or a combination thereof to a surface; exposing the composition to light; and increasing the temperature of the surface of the article when compared to a reference surface free of the composition. Maximal heat is generated when the light has a wavelength in the range of ultraviolet up to infrared. A composition of the present invention may be mixed with an adherent before or after it is applied to a surface. In addition, a composition of the present invention maybe dried, or substantially free of water, prior to being adhered to a surface. A dried composition may include microbes, bioflakes, microshells, or a combination thereof. The composition is placed between the light source and the surface.

Another embodiment of the present invention is a method of microwave protection. The method comprises the steps of applying a composition comprising melanin producing microbes, cell wall-associated melanin, extracellular vesicles comprising melanin, or a combination thereof to a surface; exposing the composition to light having a wavelength in the range of microwave radiation; and protecting the surface by inhibiting the rise of surface temperature when compared to a reference surface free of the composition. The composition is placed between the microwave radiation, or light source, and the surface. The composition maybe dried prior to being adhered to a surface.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

A "bioflake" is a lyophilized dried melanin producing microbe.

As used herein a 'fiber' is a substance that is significantly longer than it is wide that is often used in the manufacture of other materials, for example, plant fibers for use in manufacturing paper or textiles/cloths, wood fibers for use in engineered wood products or paper, animal fibers for use in textiles or clothing.

A "microshell" is a cell wall-associated melanin structure that remains after removing most cellular components.

A "reference" refers to a standard or control conditions such as a sample or surface that is free, or substantially free, of an agent such as melanin.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The terms "ultraviolet" and "UV" are used herein to mean electromagnetic radiation, especially solar electromagnetic radiation, with a wavelength from about 100 nm to about 400 nm, and includes the UV-A, UV-B, and UV-C sub-classifications of such radiation. The term "UV-A" means ultraviolet electromagnetic radiation with a wavelength from about 320 nm to about 400 nm and includes UV-A1 (from about 340 nm to about 400 nm) and UV-A2 (from about 320 nm to about 340 nm). The term "UV-B" means ultraviolet electromagnetic radiation with a wavelength from about 290 nm to about 320 nm. The term "UV-C" means ultraviolet electromagnetic radiation with a wavelength from about 200 nm to about 290 nm.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (e.g., meaning "including, but not limited to,") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

2. Isolation of Cell Wall-Associated Fungal Melanin.

Cell wall-associated melanin may be isolated from melanotic fungi yielding a melanin coat or "ghost" the size of a cell (micrometers in diameter) but this multistep process of extracting melanin from a ghost is extremely laborious. Described herein is a shorter version of the cell-wall isolation protocol that produces similar yields in shorter time at lower extraction costs (Table 1). In addition, described herein is a simple method to isolate melanin nanoparticles secreted to the extracellular environment by melanotic yeasts.

TABLE 1

Cell wall-associated and secreted melanin isolation compared to method previously described by Dadachova and Casadevall (U.S. Pat. No. 8,586,090, incorporated herein by reference) compared to the granule melanin isolation.

| Cell Wall-Associated Melanin Isolation (U.S. Pat. No. 8,586,090) | Cell Wall-Associated Melanin Isolation of the Present Invention | Secreted Melanin Granule Isolation of the Present invention |
|---|---|---|
| 1. Enzyme digestion of melanized fungi during 24 hours at 30° C. | 1. Boiling in 6N HCl for 2 hours | Ultracentrifuge a cell-free supernatant of melanotic fungal liquid culture by >100,000 × g for 30 minutes – 24 hours. Collect the sediment melanin nanoparticles. |
| 2. 4M guanidine thiocyanate for 12 hours at room temperature | 2. Folch extraction method (Chloroform: methanol:aqueous saline) mixture as 8:4:3. Repeat step for a total of 3 consecutive times. | |

TABLE 1-continued

Cell wall-associated and secreted melanin isolation compared to method previously described by Dadachova and Casadevall (U.S. Pat. No. 8,586,090, incorporated herein by reference) compared to the granule melanin isolation.

| Cell Wall-Associated Melanin Isolation (U.S. Pat. No. 8,586,090) | Cell Wall-Associated Melanin Isolation of the Present Invention | Secreted Melanin Granule Isolation of the Present invention |
| --- | --- | --- |
| 3. Proteinase K for 4 hours at 65° C. | 3. Let to air dry. Material can be wash with pure water. | |
| 4. Folch extraction method (Chloroform:methanol:aqueous saline) mixture as 8:4:3. | | |
| 5. Boiling in 6N HCl for 2 hours | | |

Provided herein are methods for purifying cell wall-associated melanin comprising the steps of heating a melanin producing microbe in 6N HCl and extracting the melanin using a chloroform:methanol:saline mixture.

The extracting step may be performed before or after the heating step. In some embodiments, the heating step is performed before the extracting step. In other embodiments the heating step is performed after the extracting step. The method may further comprise, repeating the extracting step at least once. In some embodiments, the extracting step is repeated once. In some embodiments, the extracting step is repeated twice. In some embodiments, the extracting step is repeated three times.

The heating step may have a temperature in the range of 60° C. to 120° C. In some embodiments the heating step has a temperature of at least 60° C., at least 65° C., at least 70° C., at least 75° C., at least 80° C., at least 85° C., at least 90° C., at least 95° C., at least 100° C., at least 105° C., at least 110° C., or at least 115° C. In some embodiments the heating step has a temperature less than 120° C., less than 115° C., less than 110° C., less than 105° C., less than 100° C., less than 95° C., less than 90° C., less than 85° C., less than 80° C., less than 75° C., less than 70° C., or less than 65° C.

The heating step may have a duration of 30 minutes to 24 hours. In some embodiments, the heating step may have a duration of about 30 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In certain embodiments, the heating step may have a duration from 30 minutes to 3 hours, from 30 minutes to 2.5 hours, from 30 minutes to 2 hours, from 30 minutes to 1.5 hours, from 30 minutes to 1 hour, from 1 hour to 3 hours, from 1 hour to 2.5 hours, from 1 hour to 2 hours, or from 1 hour to 1.5 hours.

The chloroform:methanol:saline mixture may be any mixture useful in the removal of lipids from a sample. A suitable mixture may have a concentration in the range of 7-10 parts chloroform:3-5 parts methanol:1-5 parts saline. In some embodiments, the mixture has a concentration of 8 parts chloroform, 4 parts methanol, and 3 parts saline by volume.

The melanin producing microbe may be any microbes capable of producing melanin. In some embodiments, the melanin producing microbe is a melanin producing fungus. The melanin producing fungus may be any of those fungal species known in the art to produce melanin either constitutively or under melanin producing conditions. In some embodiments, the melanin producing fungus is selected from the group consisting of *Cryptococcus neoformans, Aureobasidium melanogenum, Exophiala dermititidis, Cryomyces antarcticus* and *Cryptococcus* chs3, *Cryptococcus* csr2, *Cryptococcus* pgi1, modified cell wall mutants thereof, and combinations thereof. In some embodiments, the melanin producing fungus is selected from the group consisting of *Exophiala dermatitidis, Agaricus biscporus, Cladosporium sphaerospermum*, and combinations thereof. In select embodiments, the melanin producing fungus is *Cryptococcus neoformans*.

3. Isolation of Secreted Melanin Granules

A method for isolating secreted melanin granule nanoparticles may be based on ultracentrifugation of culture supernatant that may also be used for other melanotic microorganisms (FIG. 2). The granule melanin isolation methods of the present invention provide a new source of melanin material in the form of spherical nanoparticles.

Provided herein are methods of purifying extracellular melanin nanoparticles comprising providing a culture of microbes producing extracellular vesicles comprising melanin, removing the microbes from the culture forming a cell free supernatant comprising extracellular vesicles comprising melanin, sedimenting the extracellular vesicles comprising melanin, and collecting the extracellular vesicles comprising melanin.

Removing the microbes from the culture and forming a cell free supernatant may be completed by any of the methods well-known in the art. In some embodiments, removing the removing the microbes comprises centrifugation, filtration, or a combination thereof.

The method may further comprise fractionating the extracellular vesicles in a density gradient.

The microbes producing extracellular vesicles comprising melanin may include any species that secrete melanin into their extracellular environment. The microbes producing extracellular vesicles comprising melanin may be *Cryptococcus neoformans, Aureobasidium melanogenum, Exophiala dermititidis, Cryomyces antarcticus* and *Cryptococcus* modified cell wall mutants, and combinations thereof. In some embodiments, the microbes producing extracellular vesicles comprising melanin is selected from the group consisting of *Exophiala dermatitidis, Agaricus biscporus, Cladosporium sphaerospermum*, and combinations thereof. In select embodiments, the microbes producing extracellular vesicles comprising melanin is *Cryptococcus neoformans*.

4. Melanin Compositions and Coated Articles a. Melanin Compositions

Provided herein are compositions comprising melanin. The compositions comprising melanin may comprise melanin producing microbes, bioflakes, purified cell wall-associated melanin, extracellular vesicles comprising melanin, microshells or a combination thereof.

The melanin producing microbe may be selected from the group consisting of *Cryptococcus neoformans, Aureobasidium melanogenum, Exophiala dermititidis, Cryomyces antarcticus* and *Cryptococcus* chs3, *Cryptococcus* csr2, *Cryptococcus* pgi1,-modified cell wall mutants thereof, and combinations thereof. The melanin producing fungus may be selected from the group consisting of *Agaricus biscporus, Cladosporium sphaerospermum*, and combinations thereof. In select embodiments, the melanin producing fungus is *Cryptococcus neoformans*.

The melanin may be produced using the methods described herein in Sections 2 and 3.

The compositions may contain standard additives, such as thickening agents, antifoam agents, corrosion inhibitors, dispersants, binders, curing agents, crosslinkers, adherents, biocides, conditioners, fixatives, and the like. The compositions comprising melanin may be formulated, for example, as a paint, a varnish, a shellac, a glaze, an ink, a dye, a powder, and the like.

b. Melanin Coated Articles and Methods of Making a Melanin Coated Article

Provided herein are melanin coated articles. FIG. 4 shows how a L-DOPA melanized *Cryptococcus* yeast material can be dried on different surfaces (glass, plastic, and aluminum), forming a thick melanin biofilm, capturing heat from electromagnetic radiation due to the presence of melanin.

Figure 5A:
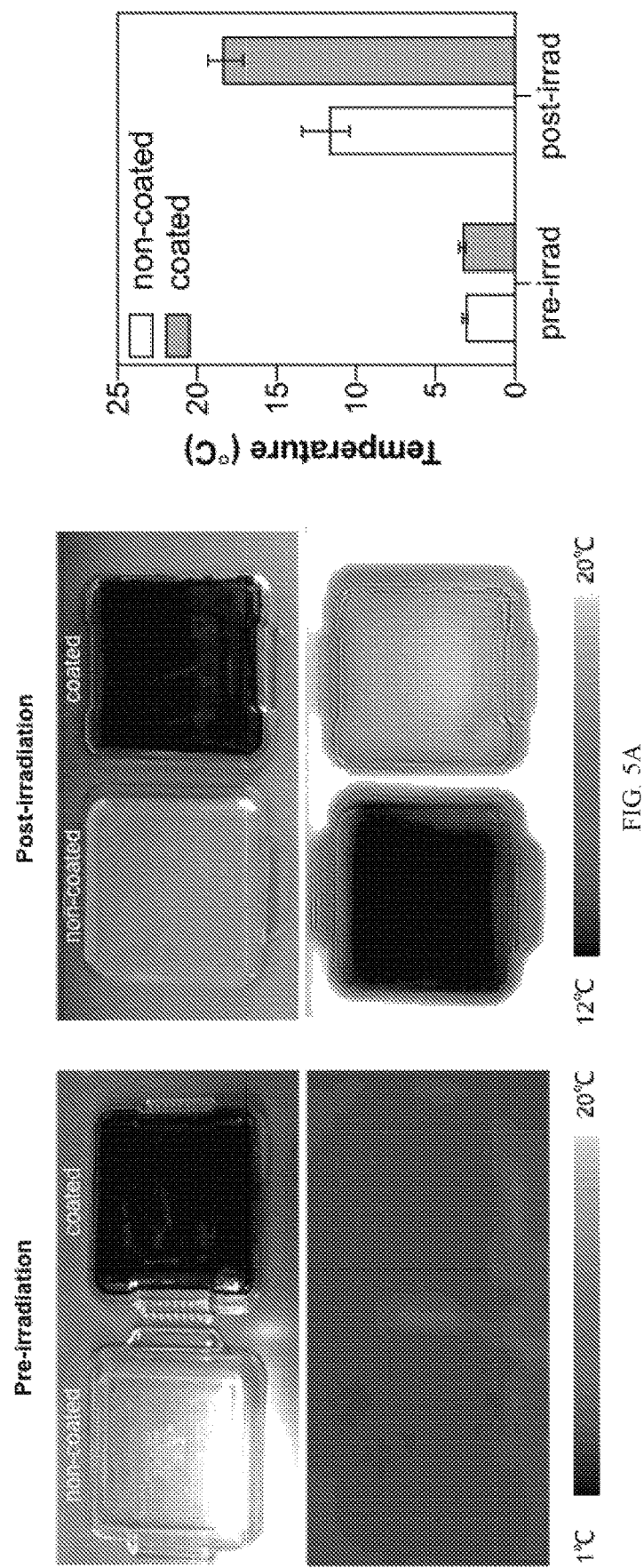
FIGS. 5A-5B illustrate light microscopy images of dehydrated melanized (FIG. 5A) and non-melanized (FIG. 5B) yeast cells in the form of flakes.
Figure 5B:
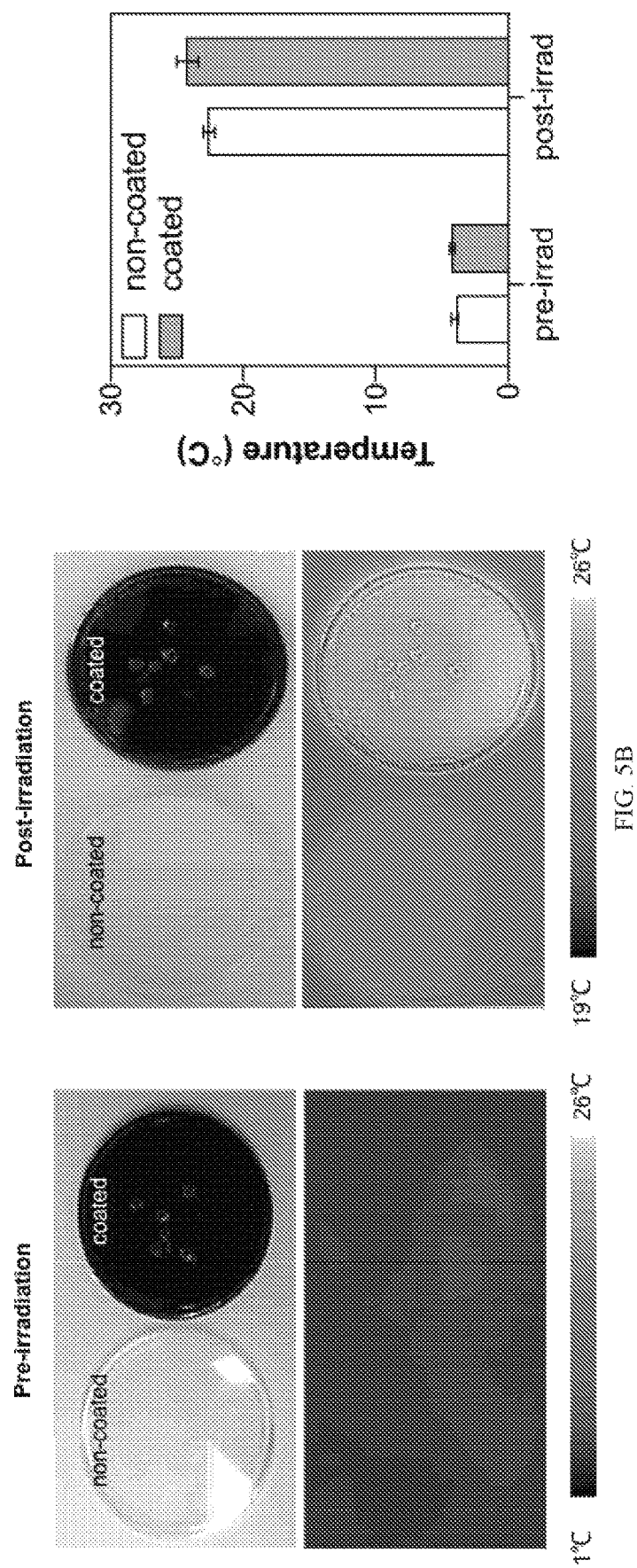
Figure 5C:
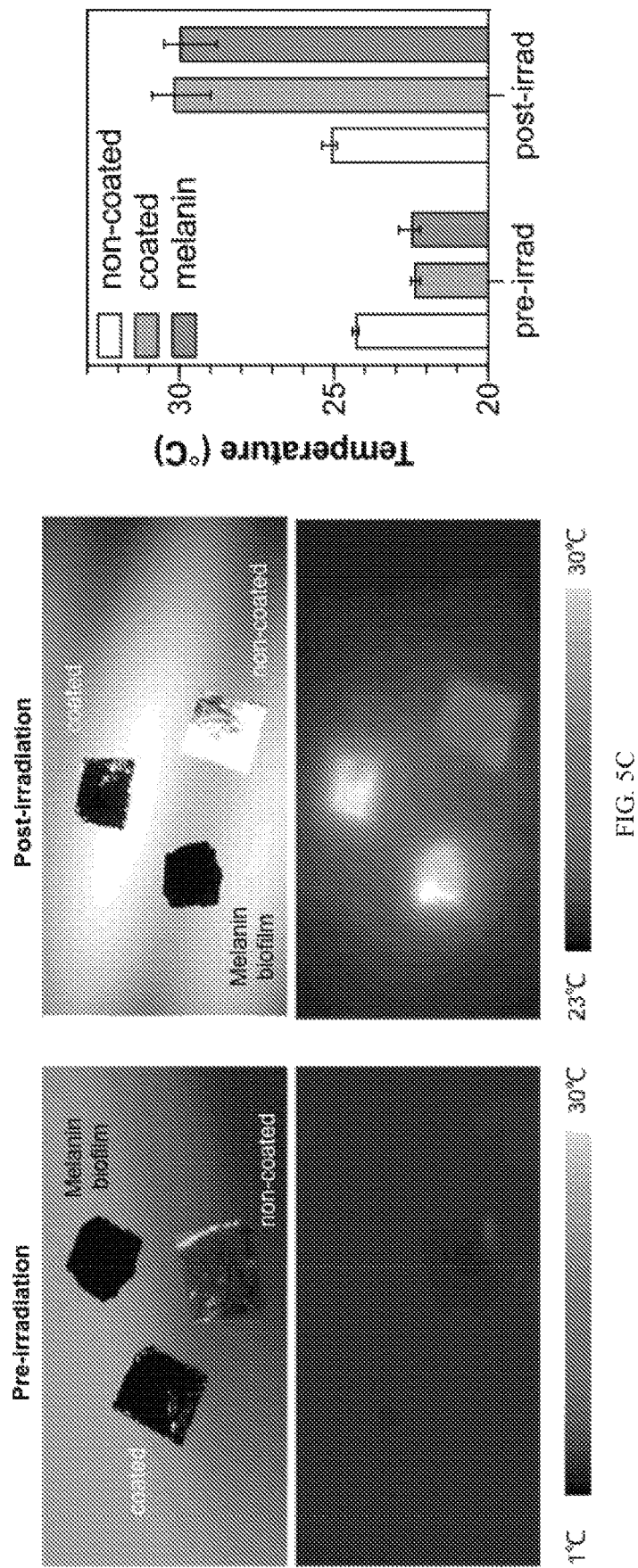
FIG. 5C illustrates light microscopy images illustrates the heat absorption capacity of melanized versus non-melanized bioflakes following 60 second of radiation.

Melanized yeasts can be dehydrated yielding flakes of biological material or bioflakes that can capture heat from radiation. For this, melanized yeast cells are grown and collected by centrifugation, and placed in a lyophilizer or freeze-drying instrument for 1-2 days (depending on the amount). These bioflakes have a metallic appearance and are also effective in absorbing heat from radiation (FIG. 5).

The melanin coated article may comprise: an article and a coating supported by the surface of the article, wherein the coating comprises a composition comprising melanin. In some embodiments, the coating covers at least a portion of the surface of the article (such as, for example at least 5%, at least 10%, at least 15%, at least 20%, at least 25%, at least 30%, at least 40%, at least 50%, at least 60%, at least 70%, at least 75%, at least 80%, at least 85%, at least 90% or at least 95% of the article). In selected embodiments, the coating covers the entire surface of the article.

The surface of the article may comprise plastic, glass, metal, wood, ceramic, aluminum, polystyrene, fibers or a combination thereof. The fibers may be animal-based, plant-based or synthetic, including, for example, silk, wool, angora, cotton, linen (flax), hemp, bamboo, wood, nylon, rayon, polyester, orlon, acetate, jute, and the like.

The composition comprising melanin may comprise melanin producing microbes, bioflakes, purified cell wall-associated melanin, extracellular vesicles comprising melanin, microshells or a combination thereof. The melanin producing microbe may be selected from the group consisting of *Cryptococcus neoformans, Aureobasidium melanogenum, Exophiala dermititidis, Cryomyces antarcticus* and *Cryptococcus* chs3, *Cryptococcus* csr2, *Cryptococcus* pgi1, modified cell wall mutants thereof, and combinations thereof. The melanin producing fungus may be selected from the group consisting of *Exophiala dermatitidis, Agaricus biscporus, Cladosporium sphaerospermum*, and combinations thereof. In select embodiments, the melanin producing fungus is *Cryptococcus neoformans*.

The cell wall-associated melanin may be produced using the methods described herein in Section 2. The extracellular melanin nanoparticles may be produced using the methods described herein in Section 3.

Also provided herein are methods of producing melanin coated articles comprising the steps of applying a composition comprising melanin to the surface of an article and drying the composition.

In some embodiments, the drying step is after the step of applying the composition to the surface. In some embodiments, the drying step is before the step of applying the composition to the surface.

In some embodiments, the method further comprises mixing the composition with an adherent. In exemplary embodiments, the adherent is a polymer (e.g., thermoplastic polymers, thermosetting polymers, pressure-sensitive adhesive polymers, epoxies, light or UV curing polymers). The adherent may be a coating material, a polyurethane, a ceramic, concrete, sealant, a lacquer, resin, or a primer.

The surface of the article may comprise plastic, glass, metal, wood, ceramic, aluminum, polystyrene, fibers or a combination thereof. The fibers may be animal-based, plant-based or synthetic, including, for example, silk, wool, angora, cotton, linen (flax), hemp, bamboo, wood, nylon, rayon, polyester, orlon, acetate, jute, and the like.

The article many include a variety of objects including, but not limited to, helmets, pill bottles, food packaging, building materials, lamps, sunshades, photoelectric devices, materials for vehicles or vehicles including military, air, and space craft, containers for plants, seeds, drugs, biological materials, radioactive materials, and the like, fabrics, umbrellas, eye-glass frames, cases for electronics, armor or equipment used for shielding specific body parts, glass windows or windshields, and clothing, fabrics, or raw fibers.

If desired, the surface can be pretreated or the composition can be combined with conventional primers, dyes or inks to improve adhesion of the composition. The thickness of the composition is a function of the solids content, viscosity of the composition and the method of application.

The composition may be applied using any of the methods known in the art including, but not limited to, conventional compressed air spray, electrostatically (e.g., powder coating), airless spray, high-volume low-pressure spraying, roller coating, brush coating, dip coating, flow coating, electrocoating, immersion, application of a thin film, and the like.

5. Melanins for Use in Radiation Energy Capture in Solar Thermal Technologies

Figure 3A:
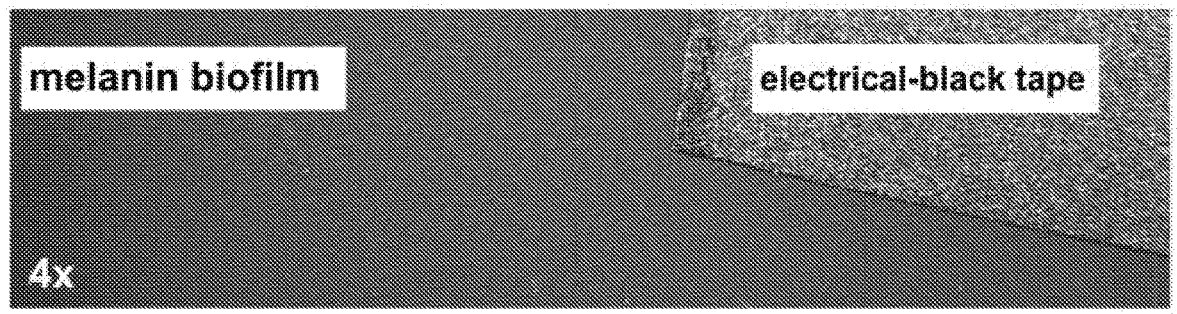
FIGS. 3A-3B illustrate a melanin biofilm coat on a polystyrene surface.
Figure 3B:
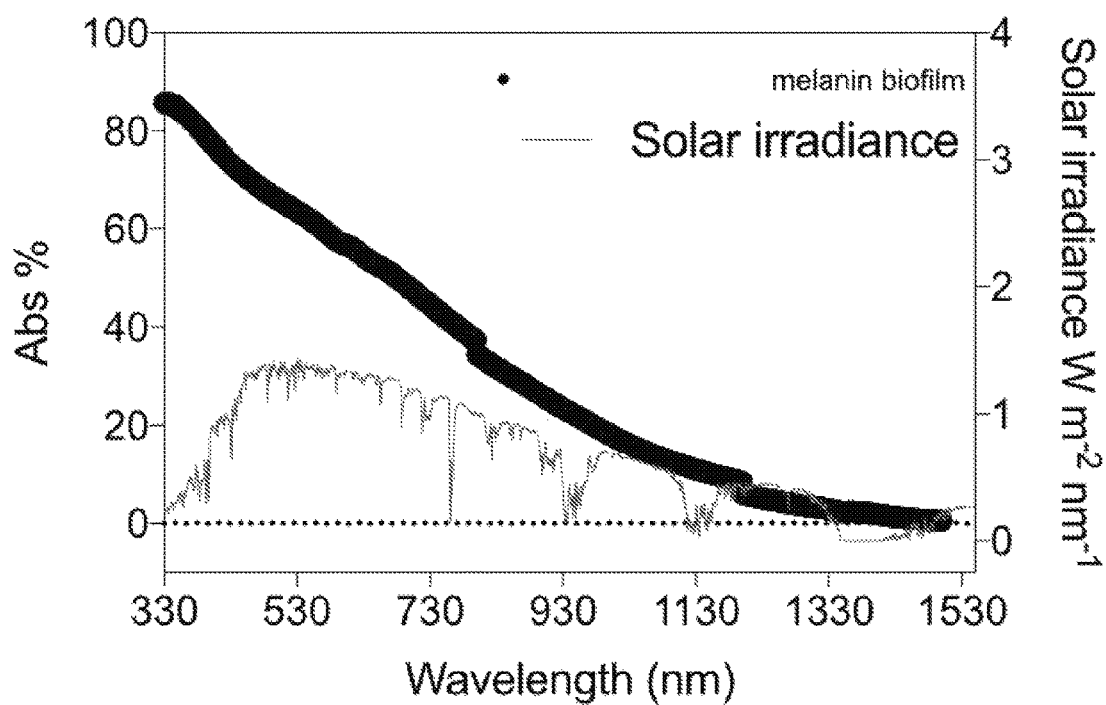
Figure 4A:
FIGS. 4A-4C illustrate the heat capture ability of fungal melanin useful to heat up a surface. Comparison between a glass (A), polystyrene (B) and aluminum (C) surfaces that are non-coated or coated with a fungal melanized biofilm. In these examples, the melanin coat is underneath the glass and polystyrene surfaces. In the aluminum example, the melanin coat is on top of the aluminum. A dried melanin biofilm was placed next to the aluminum for comparison. Thermal imaging was done previous and post 1-minute exposure to sunlight. Bars graphs represent mean apparent temperature±min/max counts.
Figure 4B:
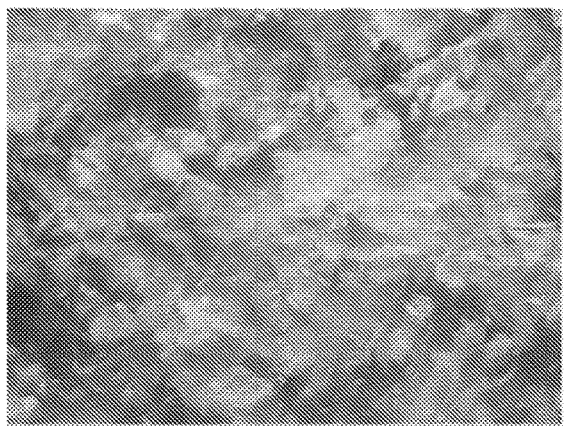
Figure 4C:
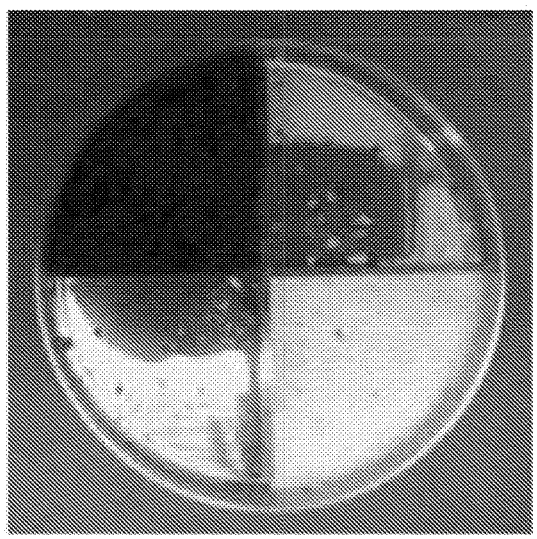
Figure 4C:
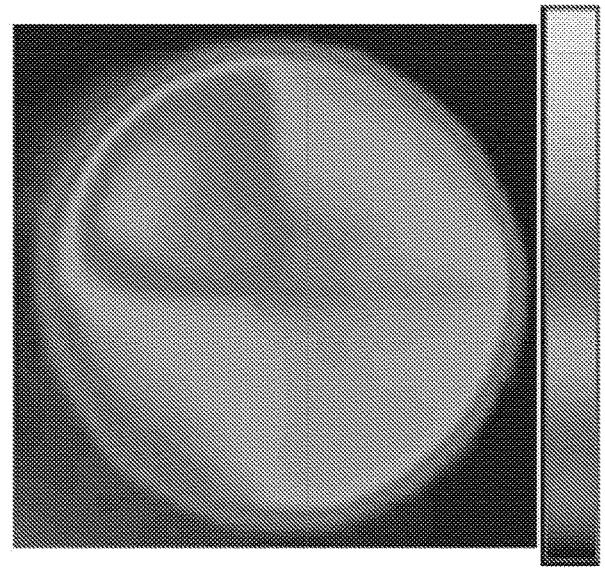

Solar absorbers are substances that convert energy from the sun into heat, hence minimizing energy investments. Melanotic yeast can capture heat from electromagnetic radiation (Cordero, R. J. B., et al., (2018) *Current Biology*); a property that can be exploited for solar thermal energy technologies. Relative to other pigments, L-DOPA melanized yeast cells exhibited the highest radiation energy conversion reaching the highest temperatures following minutes of irradiation with solar, visible, infrared and ultraviolet frequencies. Melanized yeast cells can be dried in polystyrene surfaces forming a film that can absorb >90% of all the wavelengths of light that reach Earth's surface (FIG. 3). L-Dopa melanized *C. neoformans* yeasts can be applied to surfaces resulting in a thick melanin biofilm. Melanized yeast cells are grown and collected by centrifugation as stated before, then poured on top of surface and dried under air for 1-2 days. The melanized surface will get heated up when exposed to radiation energy.

Provided herein are methods of heating an article. The method of heating an article may include providing the melanin coated article as described above in Section 4; and exposing the article to light, whereby the temperature of the article is increased.

In some embodiments, the light is ultraviolet light, infrared light, visible light, or a combination thereof.

The method may further comprise contacting the article to a material, wherein the material increases in temperature. The material may include gases, such as air, hydrogen, or propane, and fluids, such as water, fuels, and heat transfer fluids, oils, and emulsions.

6. Microbial Melanins for Microwave Radiation Shielding

The present invention relates to microbial-derived melanins as scalable and sustainable radiation energy absorbers. By way of example, *C. neoformans* is used as a melanin-producing model yeast and source of melanin to demonstrate the microwave energy damping capacity of melanin.

Figure 6A:
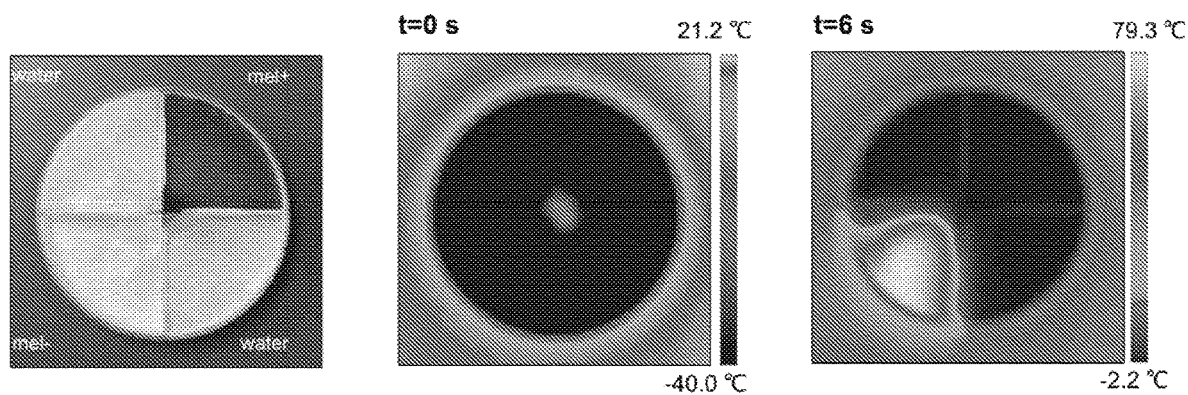
FIGS. 6A-6F illustrate the microwave shielding capacity of fungal melanin. Equal masses of ultrapure water, melanized (mel+) and non-melanized (mel−) *C. neoformans* yeasts, frozen (FIG. 6A), wet (FIG. 6B), or dried (or bioflakes) (FIG. 6C), were irradiated for various seconds inside a microwave oven (12 cm wavelength, 2450 MHz, 800 Watts) and imaged using an infrared camera.
Figure 6B:
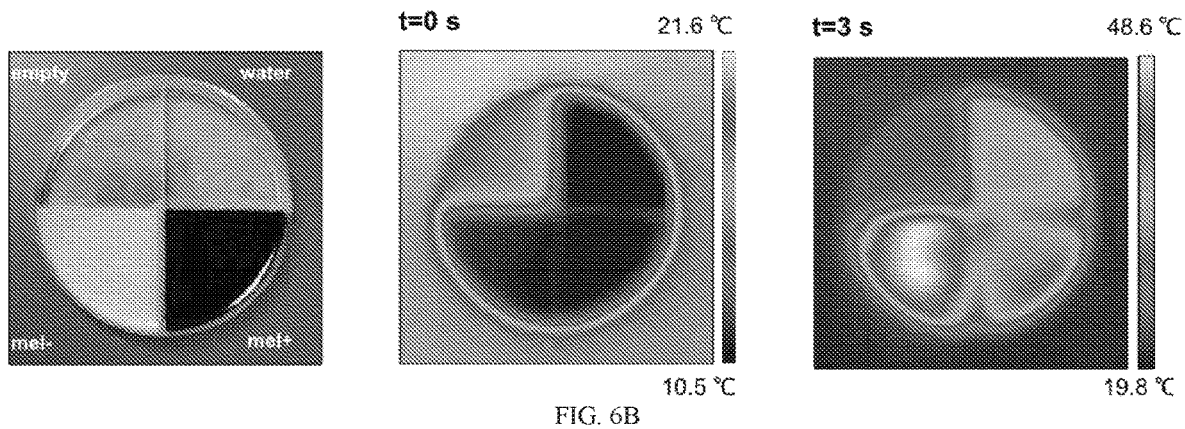
Figure 6C:
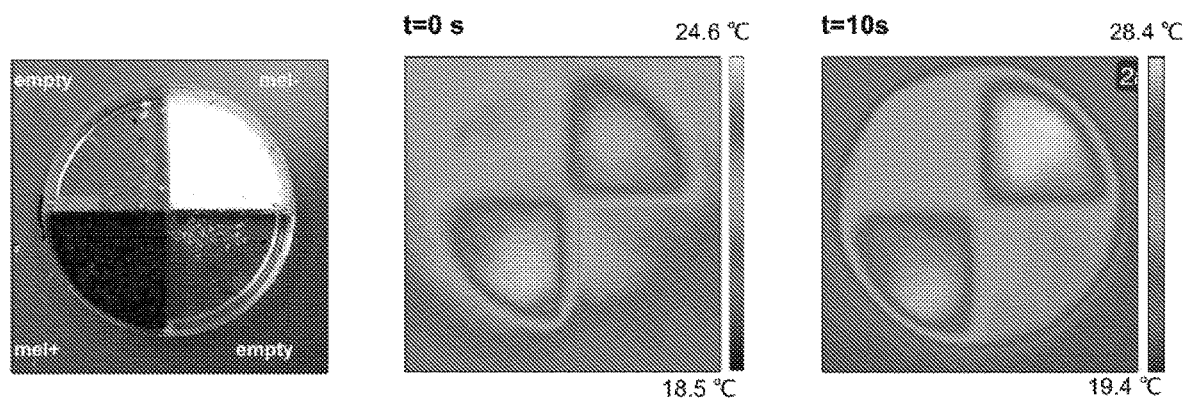
Figure 6D:
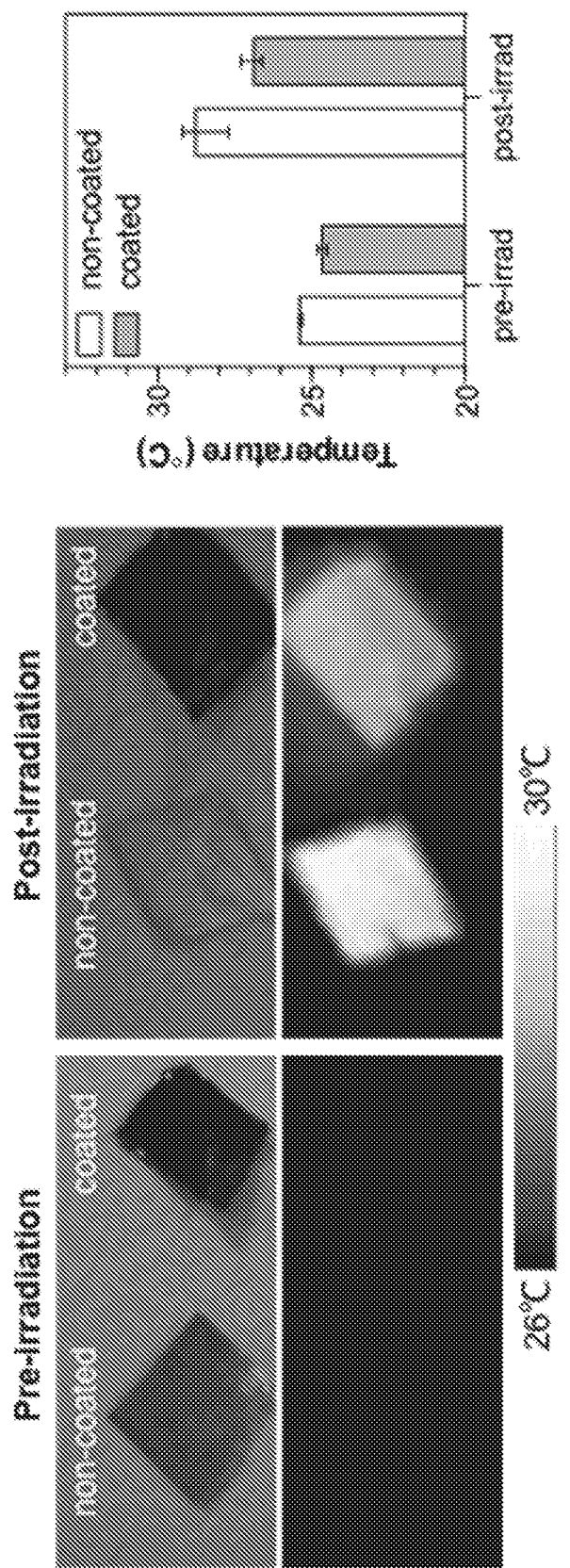
Figure 6E:
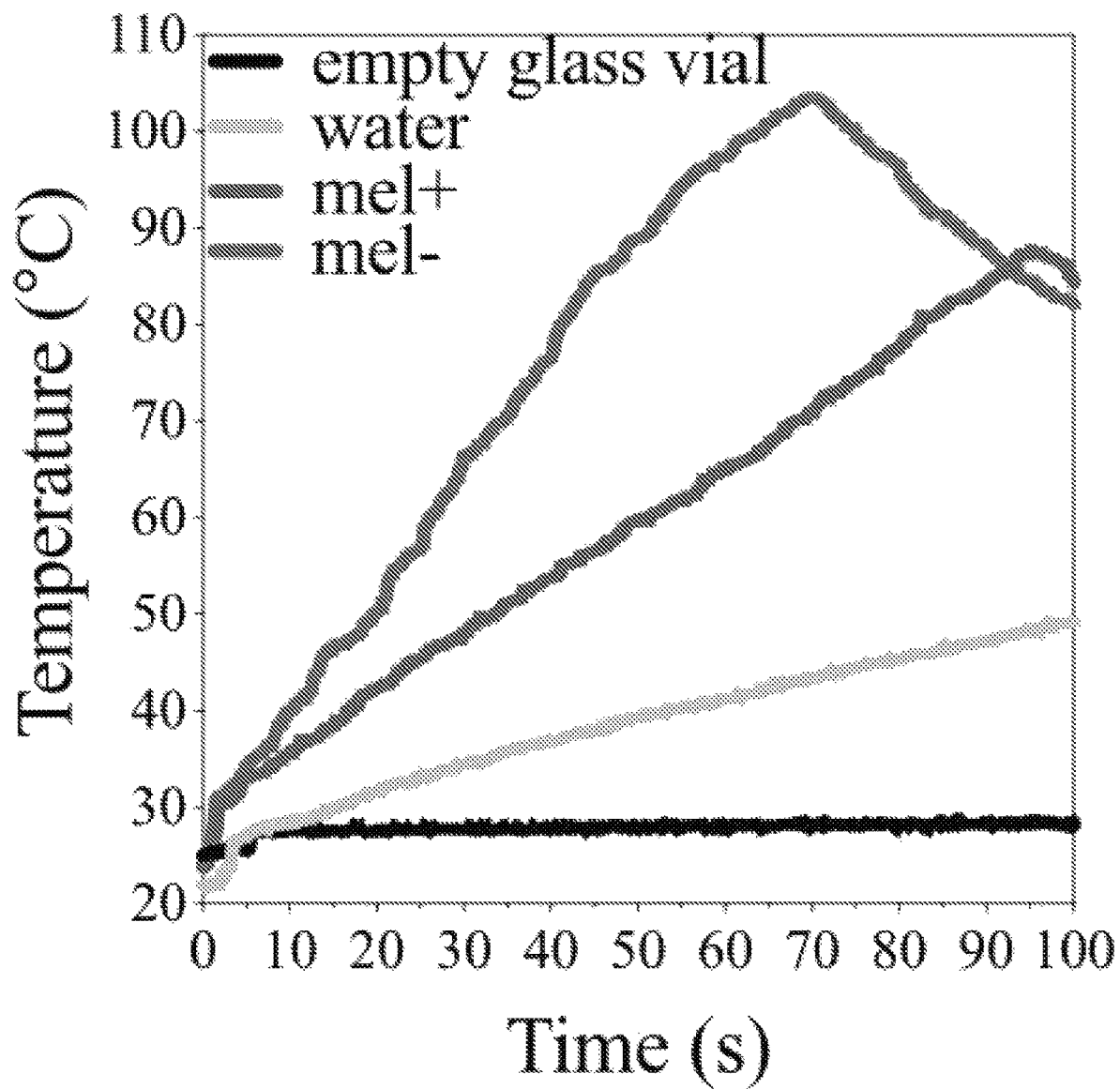
Figure 6F:
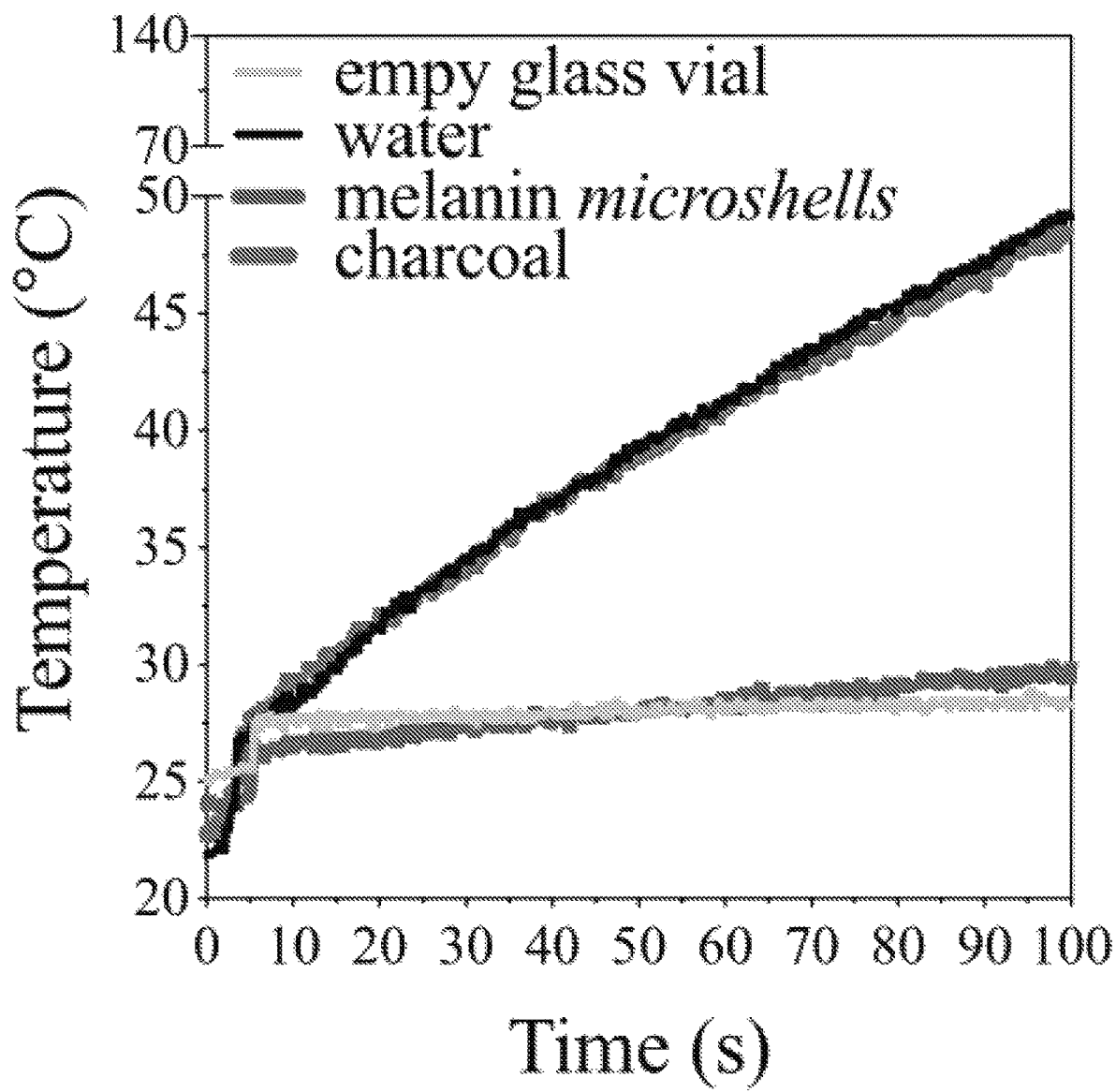

When exposed to 300-1500 nm frequencies, melanized cells show an increase in radiation absorption and temperature relative to non-melanized controls (3). In contrast to the use of melanin for solar thermal energy conversion, fungal melanin appears to dampen thermal energy following microwave exposure (FIG. 6). FIG. 6A shows relative temperatures of water, melanized yeasts and non-melanized yeast samples of *C. neoformans* following irradiation using a microwave oven. The biggest difference between melanized and non-melanized samples is observed in the frozen state. In contrast, the lowest difference is observed in the dried (bioflakes) state. A melanin biofilm coating in aluminum foil dampened heating after irradiation inside a microwave oven (FIG. 6D). Melanin and microwave interaction were confirmed using a microwave directed radiation source (FIGS. 6E & F). FIG. 6E shows the representative results obtained from equal volumes of melanized and non-melanized *C. neoformans* yeast masses irradiated at 20 Watts. Melanized yeasts cells exhibited lower temperatures and heating rates (approximately 2-fold lower). FIG. 6F shows the comparison between equal volumes of dried powdered isolated *Cryptococcus* melanin and activated charcoal microwaved at different power levels (20, 80, and 160 Watts). *Cryptococcus* melanin heated up less than water and much less than charcoal.

These observations demonstrate that melanin can interact with microwave radiation, damping the dissipation of heat. These also demonstrate that the capture and damping of microwave radiation energy by melanin depends on water activity and the water-melanin interaction.

A scalable and cost-effective method for fungal melanin isolation will enable a variety of industrial applications based on melanin.

The heat absorption capacity of fungal melanins and melanin biofilms when exposed to UV, visible, and infrared radiation can be applied in solar thermal technologies (e.g., solar heating, solar thermal electricity generation, solar thermoelectric, and solar thermophotovoltaics). Due to the broadband optical absorption of melanins, surfaces in close contact with melanin or containing melanin can be heated up passively or without the need to spend energy. Melanin-assisted heating can be mixed or applied in spacecraft's surfaces, paintings, lacquers, coatings or construction materials in extraterrestrial spaces for passive heating. Isolated melanin, melanin biofilms and/or bioflakes can be used as solar absorbers. The use of melanotic microorganisms is also attractive given the ability of some species to survive extreme environmental conditions (cold, salt, radiation, extracellular space) and grow in the form of melanotic biofilms which can be used to coat multiple surfaces.

Due to the microwave shielding capacity of *C. neoformans* cell-wall melanin, external microwave melanin shielding can be applied for military defense applications. Melanin-containing surfaces will be thermally protected from microwave irradiation.

Any compositions or methods provided herein can be combined with one or more of any of the other compositions and methods provided herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Materials and Methods

Growth and melanization of *C. neoformans*. *C. neoformans* Serotype A strain H99 (ATCC 208821) was pre-cultured from frozen stocks in Sabouroaud dextrose liquid media for 2 days at 30° C. (shaking at 180 rpm). Pigmentation of *C. neoformans* cultures were prepared by inoculating a final concentration of $10^5$ cells/mL to sterile filtered minimal media (15 mM dextrose, 10 mM $Mg_2SO_4$, 29.3 mM $KH_2PO_4$, 13 mM glycine, 3 mM thiamine-HCL; adjusted to pH 5.5) with or without 1 mM supplementation of each pigment precursor: L-DOPA, methyl-DOPA, dopamine hydrochloride, norepinephrine, epinephrine, serotonin. Yeast cultures are grown under dark conditions for 5 days at 30° C. and shaking at 180 rpm. Yeast cells were then washed three times with PBS by decanting the supernatant after centrifugation (15 min at 6,000 rpm). The resulting melanized yeast concentrated slurry can be processed to isolate the cell wall-associated melanin, lyophilized to form bioflakes or poured on surfaces to form biofilm coat.

Melanized "bioflakes". Melanized yeast cells are collected by centrifugation, washed three times with PBS by centrifugation. Yeast pellets are freeze at −20° C. and lyophilized in a freeze-drying system (Labconco, Kansas City, MO).

Example 1

A Simple, Cost Effective Method for Isolating Melanin from the Cell Wall

The inventors designed a melanin extraction method that yields hollow micrometer spheres or microshells (FIG. 1) with only two steps, a method that is cost effective and speedy. Conventional melanin extraction methods are comprised of at least 5 steps wherein the first three steps of the conventional process must come before the new two-step process of the present invention as described in Table 1. The two-step process of the present invention is performed without the conventional steps of enzyme digestion, 4M guanidine thiocyanate, and proteinase K as shown in Table 1.

Cell wall melanin isolation. One liter of melanized *C. neoformans* culture was harvested by centrifugation (15 min at 4,500 rpm) and washed twice with PBS. The yeast pellet was suspended with equal volume of 6 N HCl and incubated 1 hour at 100° C. Hydrolyzed material was washed three times with PBS and subjected to 3 consecutive Folch lipid extractions maintaining final mixtures to 8:4:3 chloroform:methanol:saline-solution. The methanol-aqueous upper fraction containing melanin was collected and centrifuged at 4,000 for 5 mins. The precipitated melanin pellet is set to air dry that result into a packed pellet. Alternatively, the extracted melanin particles can be dialyzed against distilled water overnight and lyophilized in a freeze-drying system (Labconco, Kansas City, MO).

Figure 1C:
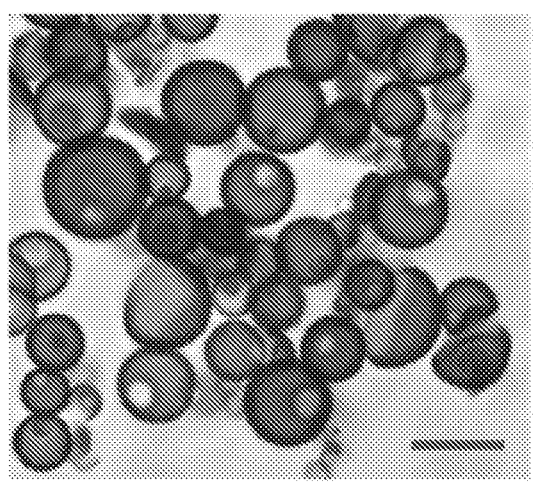
Figures 1D, 1E:
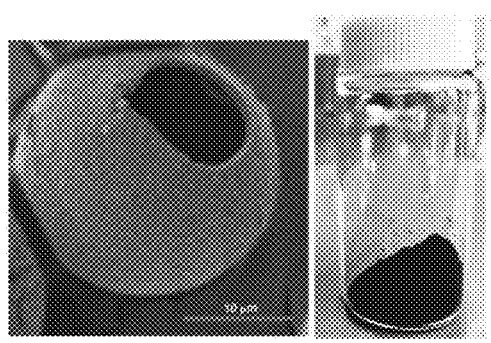
Figure 1F:
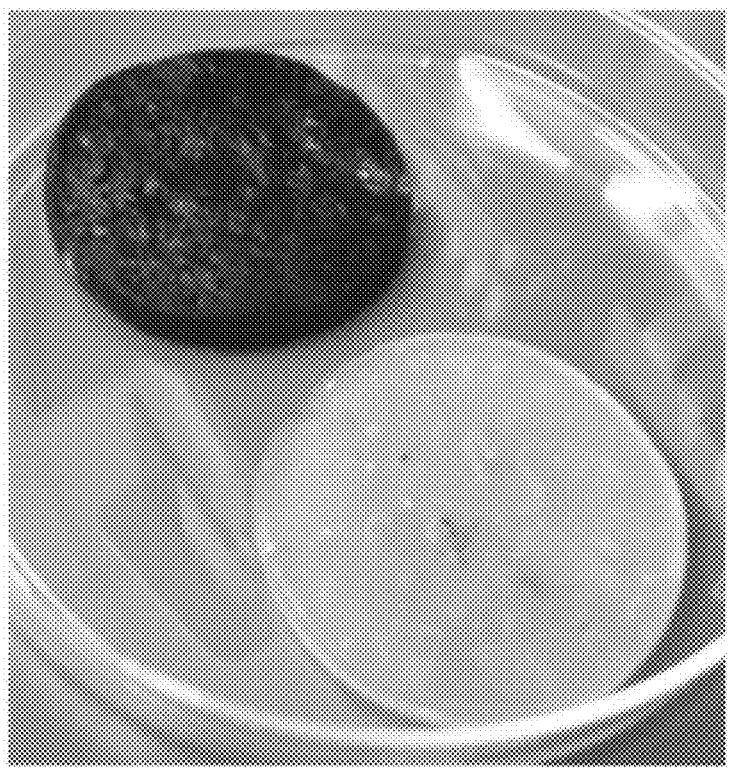

The two-step process begins by growing the fungi in a growth medium such as 15 mM dextrose, 10 mM $Mg_2SO_4$, 29.3 mM $KH_2PO_4$, 13 mM glycine, 3 mM thiamine-HCl; adjusted to pH 5.5 with or without 1 mM supplementation of each pigment precursor (e.g. L-DOPA) for 2-14 days (FIG. 1A). Melanized yeast cells (FIG. 1B) are collected by centrifugation and subjected to acid hydrolysis followed by an organic extraction consisting of 8:4:3 mixture of chloroform:methanol:aqueous saline. The process recovers cell wall-associated melanin in the form of microshells (FIGS. 1C&D). These melanin microshells exhibit a broad-band monotonic absorption spectrum which is typical to melanins covering the whole solar irradiance range (FIG. 1F).

Example 2

A Simple, Cost Effective Melanin Extraction Method by Isolating Yeast Extracellular Melanin Nanoparticles This method was developed when the inventors surprisingly discovered that some fungi secrete fungal melanin granules or nanoparticles into their growth media or supernatant. The inventors determined cultured supernatants of melanized *C. neoformans* provide a source of disperse melanin nanoparticles or extracellular granules that can be easily isolated by ultracentrifugation (FIG. 2). Such that, *C. neoformans* is one example of a suitable melanin granule producing fungus used in the present invention. Normal wildtype strains secrete melanin granules by other suitable microbes used in the present invention include several mutants [chs3, csr2, pgi1] of *Cryptococcus* having modified cell wall components (e.g., chitin, chitosan) that further increase the secretion of these melanin nanoparticles ('leaky' mutants) or disturbing the cell wall with dye molecules. All of these microbes may be used in the methods of the present invention.

Figure 2A:
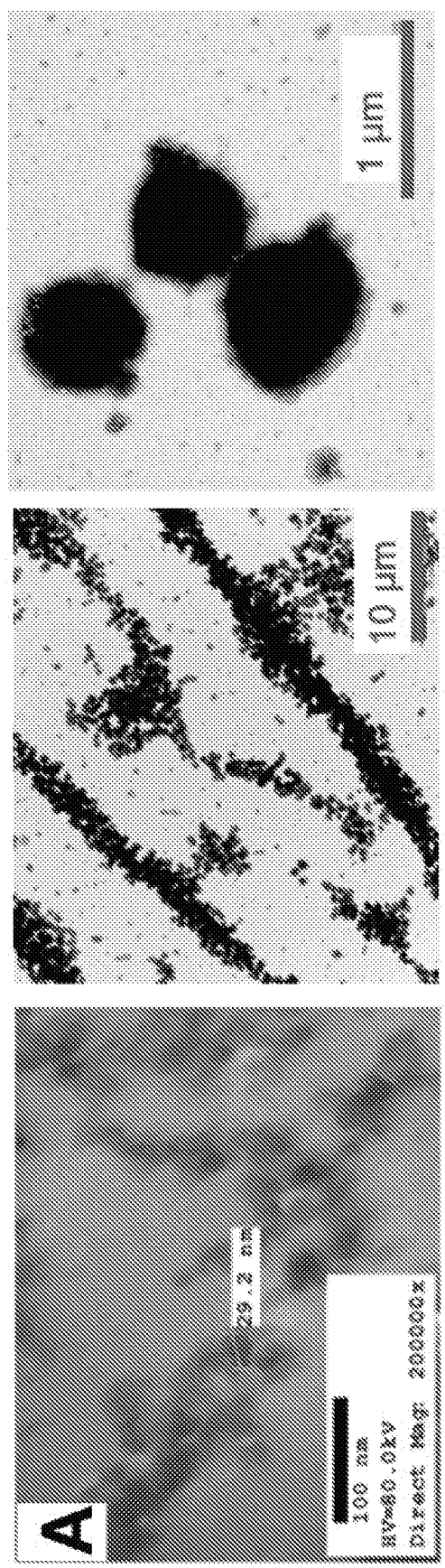
FIGS. 2A-2D illustrate characteristics of extracellular melanin vesicles, granules or nanoparticles isolated from *C. neoformans*.
Figure 2B:
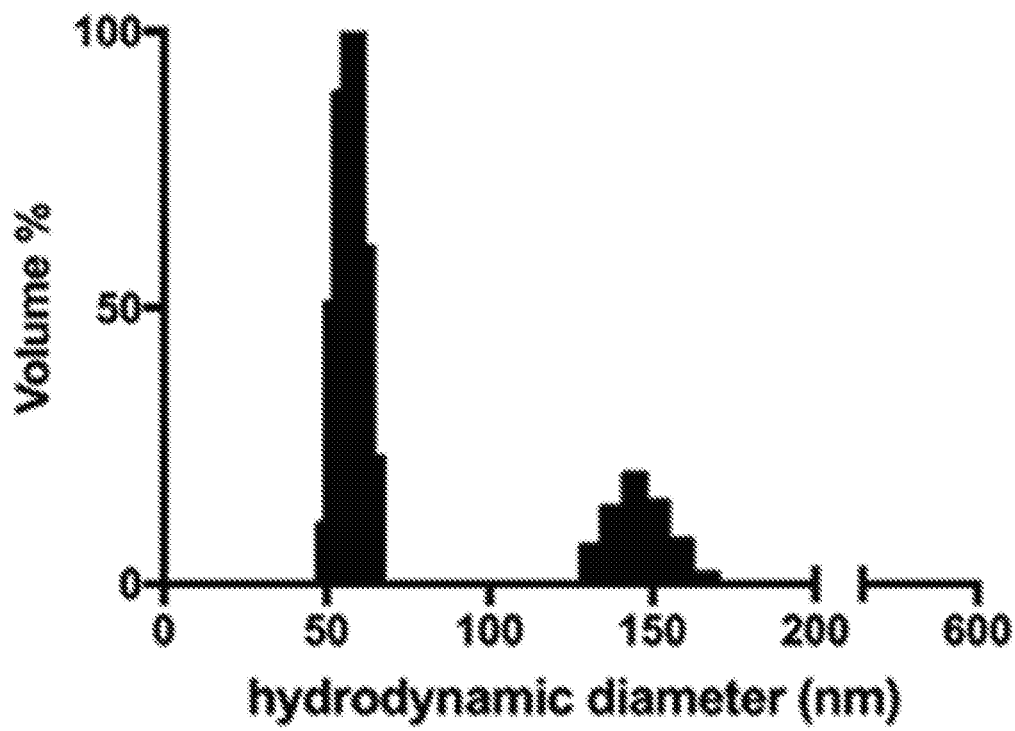
Figure 2C:
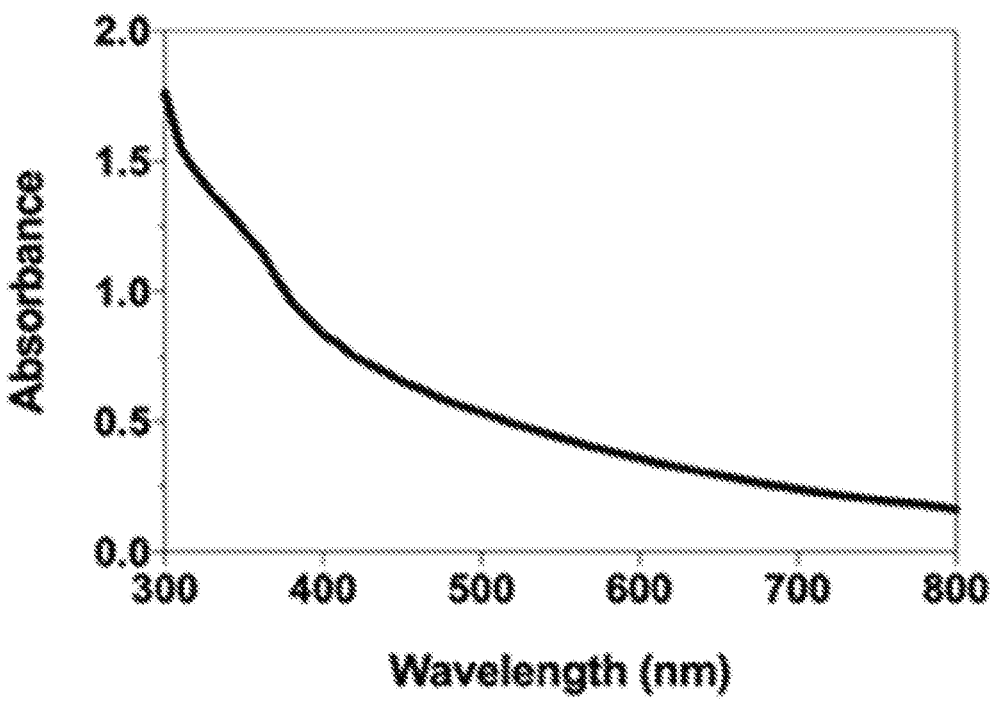
Figure 2D:
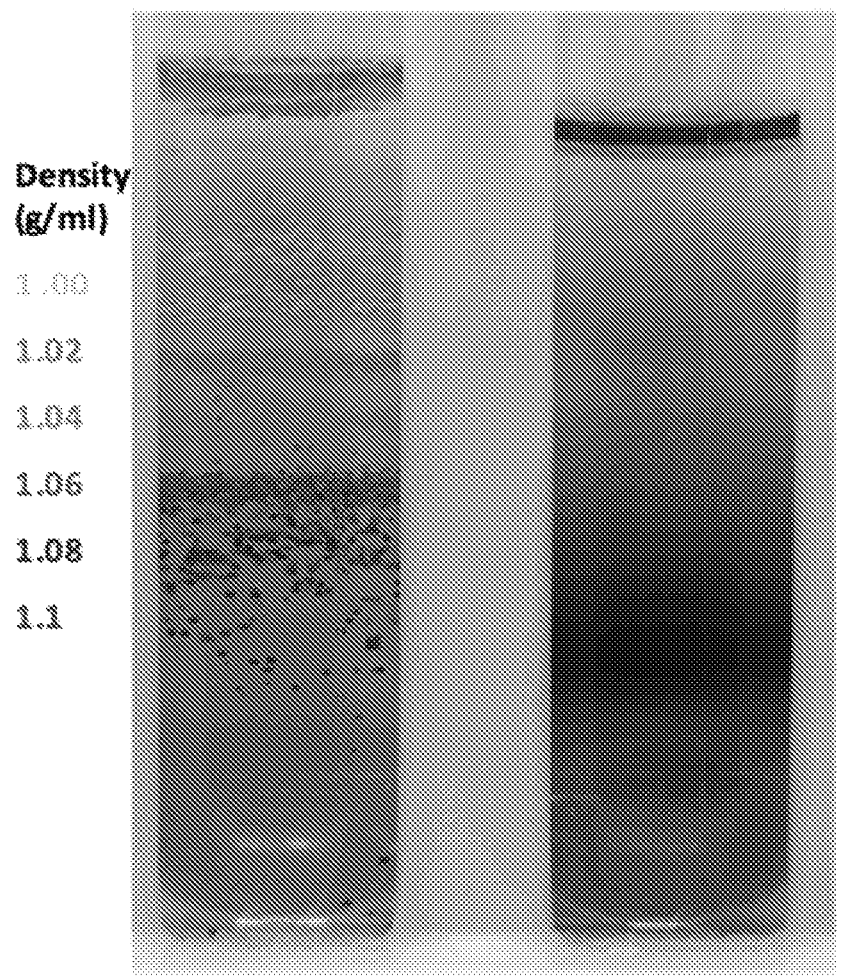

Fungal melanin granules produced by *C. neoformans* are typically spherical melanin nanoparticles that can be isolated from growth media by ultracentrifugation (100,000×g). If necessary, the granules may be further purified using density gradients (FIG. 2D).

Isolation of extracellular melanin nanoparticles or granules. The granule melanin isolation begins by growing the cells in a growth medium such as 15 mM dextrose, 10 mM $Mg_2SO_4$, 29.3 mM $KH_2PO_4$, 13 mM glycine, 3 mM thiamine-HCL; adjusted to pH 5.5 with or without 1 mM supplementation of each pigment precursor (e.g. L-DOPA) for 2-14 days. The cells are removed by centrifugation (4700×g for 15 minutes) and the supernatant is collected and filtered through a 0.22 micrometer membrane to ensure removal of all the yeast cells. The filtered supernatant is ultracentrifuged at 100,000×g for 1 hour and the pellet formed is melanin nanoparticles. As shown in FIG. 2A, electron microscopy revealed rounded particles ranging from 30-60 nm in diameter. Dynamic light scattering (DLS) revealed a dominant monodisperse population of particles with a hydrodynamic diameter of approximately 50 nm (FIG. 2B). Melanin granules exhibited broad-band optical absorption spectra which is typical of melanins (FIG. 2C). This melanin pellet can be further purified using a density gradient (e.g., Percoll, Optiprep) (5, 10, 20, 45%) equilibrated in 0.85% NaCl, 10 mM HEPES, pH 7.4 (FIG. 2D). Ultracentrifugation was done at least 40,000 rpm for at least 30 minutes.

Example 3

Melanin Coating

A concentrated slurry of melanin producing microbes, isolated cell wall-associated melanin, isolated extracellular vesicles comprising melanin, or a combination thereof; are applied on a surface (e.g., glass, polystyrene, aluminum) and air dried to form a melanin biofilm coat.

Thermal response to irradiation. Wet or dried yeast material was weighed on plates to control for the mass. Samples are first equilibrated at 4° C. for a minimum of 2 h and kept inside an ice-cold Styrofoam insulation box prior to irradiation. The cooling was done to maximize the temperature range between initial and final conditions. All irradiation was done by placing the sample under a light source. Solar irradiation was done by placing the sample plate over a white Styrofoam platform exposed to direct sunlight (without cloud interference and keeping the plate perpendicular to incoming rays to ensure even irradiation on sample) while monitoring an average luminance using a Light Meter (Fisher Scientific) and ambient temperature using a thermocouple. All solar irradiations were done at noon latitude 39.29, longitude 76.59. Irradiation experiments with artificial light sources were performed at the benchtop in a temperature-controlled room (22±5° C., 50% relative humidity). Infrared irradiation was performed using a heat lamp (120V/250 Watts, LR58060) placed at 50 cm above the sample plate averaging 70,000 LUX.

Thermography. Following irradiation, samples were immediately placed and imaged inside a white Styrofoam box (30×27×30 mm, 3.5 mm wall thickness) with a perforated lid to fit a FLR C2 IR camera lens (FLIR Systems, Wilsonville, OR) set at 2.5 cm distance from sample and adjusted emissivity to 0.95. Apparent temperatures of yeast samples were obtained from IR images using the FLIR Tool analysis software Version 5.13.17214.2001. Data from all irradiations was presented as mean apparent mean temperature±SD obtained from at least two individual experiments.

Spectroscopy. Melanized and non-melanized yeast wet pellets (~0.2 mL) were loaded on polystyrene lids (P35GC-0-14-C, MatTek Corp) and dried overnight at room temperature resulting in a thin biofilm. Absorption and reflection measurements were obtained using an Agilent Cary 5000 UV-Vis-NIR spectrophotometer. For accuracy, reflectance measurements were performed in an integrating sphere at an off-normal angle for specular reflection collection.

Thermal response to microwave irradiation. Equal masses of wet or freeze-dried yeast material were weighed on 4-sectioned polystyrene Petri dishes. In some cases, ultrapure water was included as deference material. Samples were first equilibrated at 4° C. for a minimum of 2 hours to maximize the temperature range between initial and final conditions. In some cases, the wet yeast samples were freeze down by placing the plate inside a Styrofoam container with a thin layer of liquid nitrogen. Samples were irradiated inside a microwave oven (12 cm wavelength, 2450 MHz, 800 Watts). The plate was quickly removed from the microwave and imaged inside a Styrofoam box, in a process that took approximately 3 seconds (delay acquisition time). To confirm equivalent irradiation to both melanized and non-melanized samples, the experiment was repeated by changing the relative position of the plate. In addition to a microwave oven, directed microwave irradiation was done using a Biotage® Initiator. Irradiation was done by placing equal volumes of melanized or non-melanized yeast cells or isolated melanin inside glass tubes exposed to 20 Watts of microwaves for 2 minutes. The Biotage instrument monitors the temperature increase from the infrared counts emitted by the irradiated sample and glass surface.

Example 4

Purification and Characterization of Melanin from Various Melanotic Fungi

Figure 7:
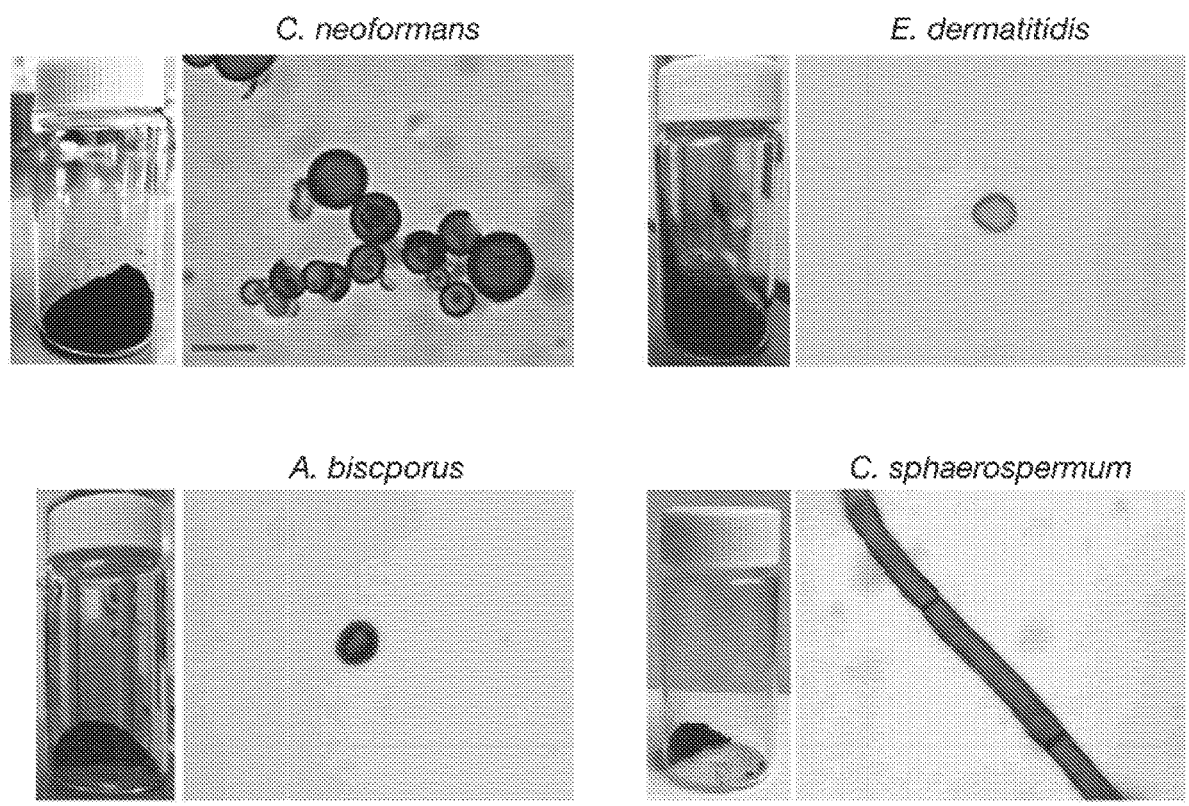
FIG. 7 are light micrographs of melanin isolated from *Cryptococcus neoformans, Exophiala dermatitidis, Agaricus biscporus, Cladosporium sphaerospermum*. Scale bar, 10 μm.

Melanin was isolated from *Exophiala dermatitidis, Agaricus biscporus, Cladosporium sphaerospermum* (FIG. 7). *E. dermatitidis* was grown in Sabouraud's agar plates and incubated at 30° C. *A. biscporus* mushrooms were purchased from the market. The filamentous fungus, *Cladosporium*, was grown in Sabouraud's agar plates and incubated at 24° C. Cells were collected from plates, and melanin isolation was performed as described in Example 1. Similar to *Cryptococcus*, the melanin isolation protocol yielded hollow melanin micrometer size particles for *Exophiala* and *Agaricus*. Melanin isolated from *Cladosporium* had a tubular structure.

Figure 8:
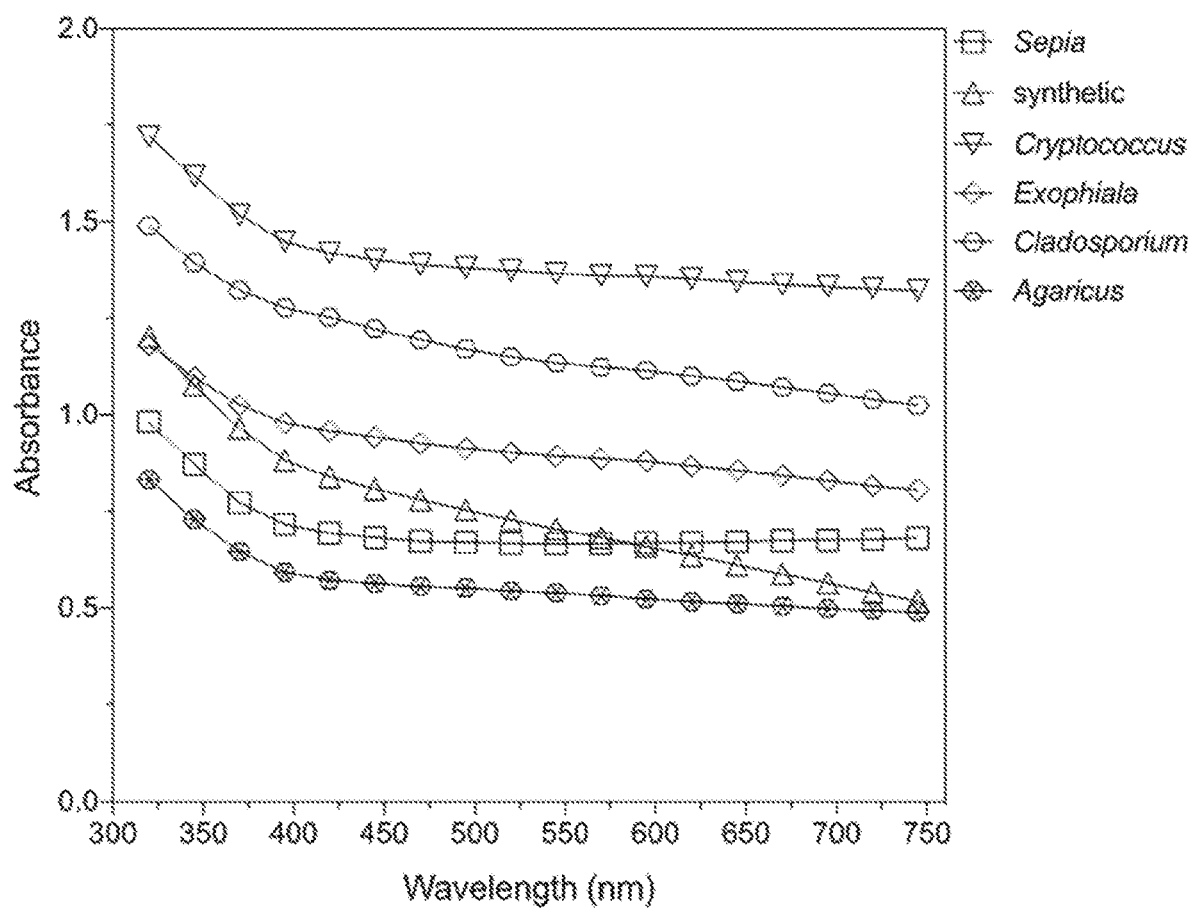
FIG. 8 is a graph of the optical absorption spectra of melanin samples isolated from *Cryptococcus neoformans, Exophiala dermatitidis, Cladosporium sphaerospermum,* and *Agaricus biscporus* in comparison with *Sepia officinalis* and synthetic melanin.

To measure the optical absorption, ten milligrams of melanin powder isolated from each of the fungal sources were suspended in 1 mL of phosphate buffer solution and optical absorption was determined using a spectrometer. Sepia (M2649) and synthetic (M8631) melanin were purchased from Sigma-Aldrich for comparison. The isolated melanin from different melanotic fungal sources showed broadband optical absorption spectra (FIG. 8) typical of melanin.

Figure 9A:
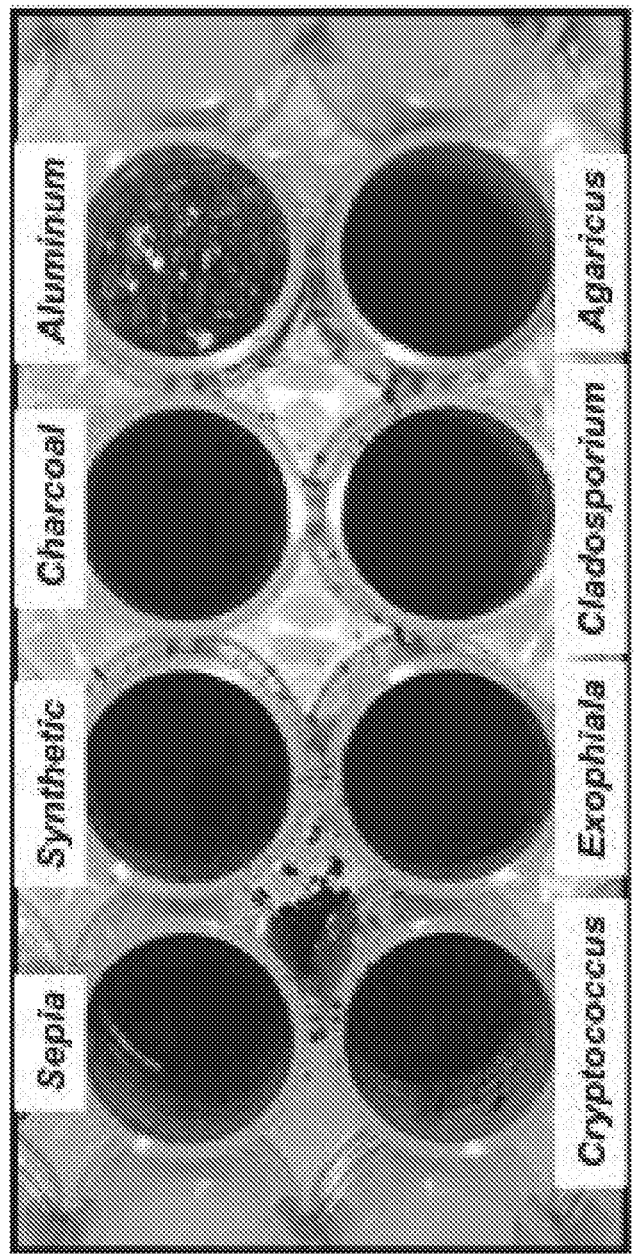
FIG. 9A and FIG. 9B show the heat capture by melanins isolated from various fungal sources.
Figure 9B:
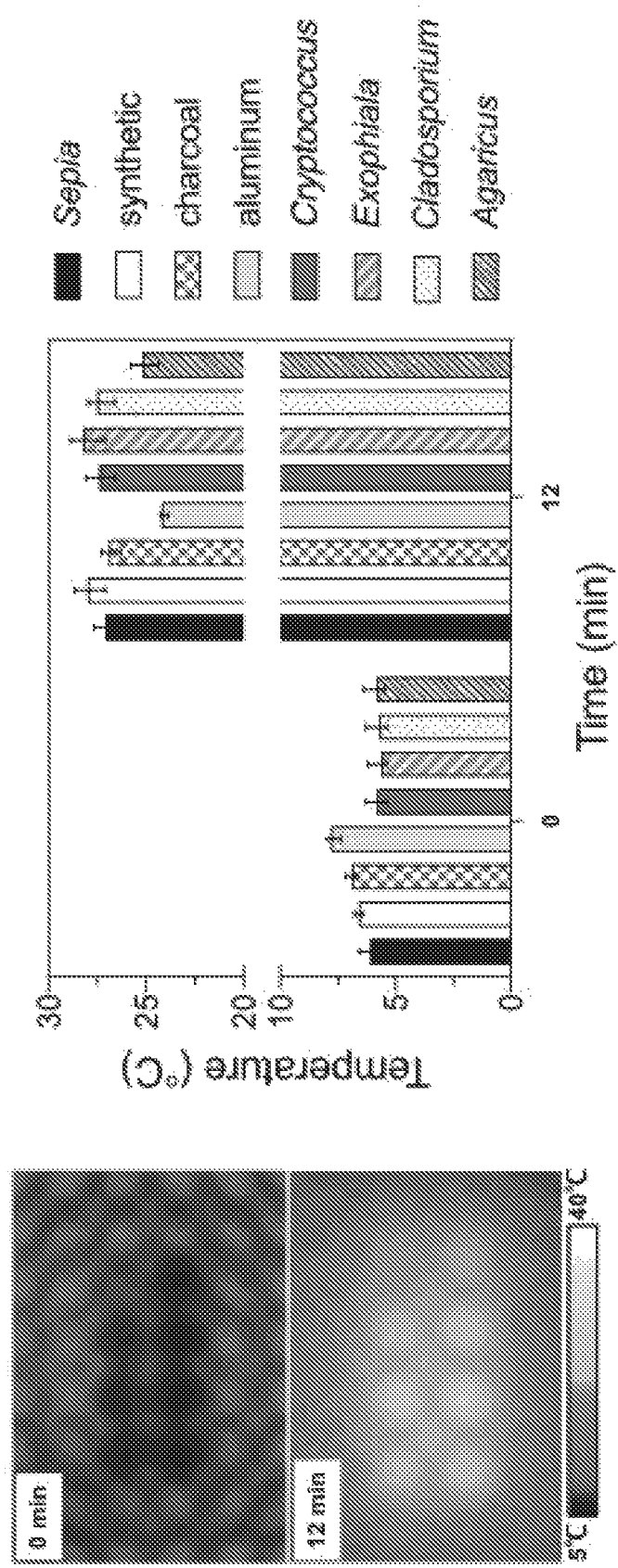

To measure the ability of the isolated melanins to capture heat from visible light, fifty milligrams of the isolated melanin powder was loaded in 48-well microtiter plates with equal masses of charcoal and aluminum foil for comparison. Samples were equilibrated at 4° C. before exposure to a white LED lamp for 12 minutes. As shown in FIG. 9, all melanin powders increased in temperature following twelve minutes of radiation exposure.

Figure 10:
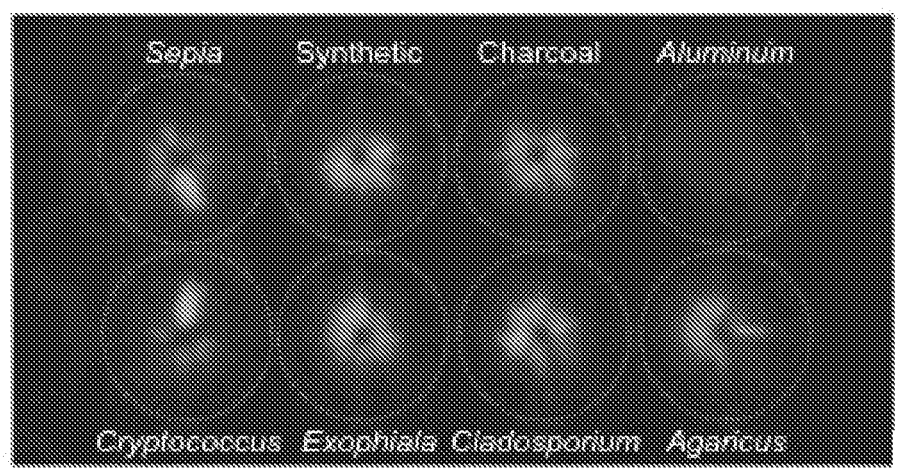
FIG. 10 shows that melanin isolated from different fungal sources can shield against ultraviolet radiation measured using radiography. The upper panel shows an image of the digital scan quantifying color intensity on shielded areas (light color means more shielding) The graph shows the quantification of color change as the mean gray value. Bars represent minimal and max modal values.
Figure 10:
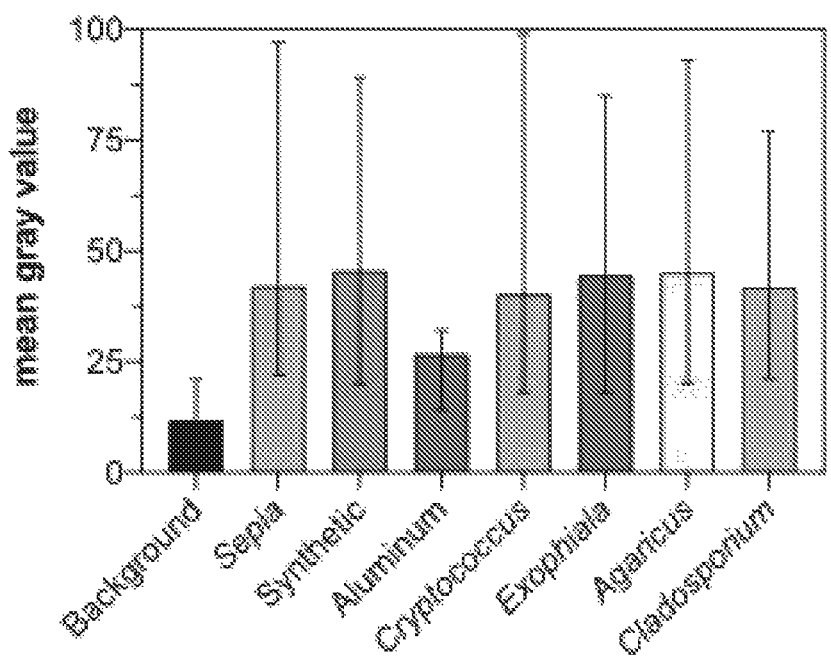

The ability of the isolated melanins to shield against ultraviolet radiation was also tested. The isolated melanin (50 mg) was placed on top of a radiography film and irradiated for 1 min with a ~280 nm UV lamp inside a Faraday box designed to control light intensity. Following irradiations, the film was developed and digitally scanned to quantify the change in color intensity on shielded areas. All the melanin powders also shielded against UV radiation (FIG. 10).

All references, including publications, patent applications, and patents, cited herein are hereby incorporated by reference to the same extent as if each reference were individually and specifically indicated to be incorporated by reference and were set forth in its entirety herein.

For reasons of completeness, various aspects of the invention are set out in the following numbered clauses:

Clause 1. A method of purifying cell wall-associated melanin comprising the steps of:
  heating a melanin producing microbe in 6N hydrochloric acid (HCl); and
  extracting the melanin using a chloroform:methanol:saline mixture.

Clause 2. The method of clause 1, wherein the heating steps are performed before the extracting step.

Clause 3. The method of clause 1 or clause 2, wherein the heating step has a temperature in the range of 60° C. to 120° C.

Clause 4. The method of any of clauses 1-3, wherein the heating step has a duration in the range of 30 minutes to 24 hours.

Clause 5. The method of any of clauses 1-4, wherein the heating step has a duration of 30 minutes to 3 hours.

Clause 6. The method of any of clauses 1-5, wherein the chloroform:methanol:saline mixture has a concentration of about 8 parts chloroform, about 4 parts methanol: and about 3 parts saline.

Clause 7. The method of any of clauses 1-6, further comprising repeating the extracting step at least once.

Clause 8. The method of clause 7, wherein the extracting step is repeated twice.

Clause 9. The method of any of clauses 1-8, wherein the melanin producing microbe is a melanotic fungi.

Clause 10. The method of any of clauses 1-8, wherein the melanin producing microbe is selected from the group consisting of *Cryptococcus neoformans, Aureobasidium melanogenum, Exophiala dermititidis, Cryomyces antarcticus* and *Cryptococcus* chs3, *Cryptococcus* csr2, *Cryptococcus* pgi1, modified cell wall mutants thereof, *Agaricus biscporus, Cladosporium sphaerospermum*, and combinations thereof.

Clause 11. A method of purifying extracellular melanin nanoparticles comprising the steps of:
  providing a culture of microbes producing extracellular vesicles comprising melanin;
  removing the microbes from the culture forming a cell free supernatant comprising extracellular vesicles comprising melanin;
  sedimenting the extracellular vesicles comprising melanin; and
  collecting the extracellular vesicles comprising melanin.

Clause 12. The method of clause 11, wherein removing the microbes comprises centrifugation, filtration, or a combination thereof.

Clause 13. The method of clause 11 or clause 12, wherein the method further comprises fractionating the extracellular vesicles in a density gradient.

Clause 14. The method of any of clauses 11-13, wherein the microbes producing extracellular vesicles comprising melanin comprise *Cryptococcus neoformans, Aureobasidium melanogenum, Exophiala dermititidis, Cryomyces antarcticus* and *Cryptococcus* chs3, *Cryptococcus* csr2, *Cryptococcus* pgi1, modified cell wall mutants thereof, *Agaricus biscporus, Cladosporium sphaerospermum*, and combinations thereof.

Clause 15. A composition comprising melanin produced by the method of any one of clauses 1-14.

Clause 16. A method of producing a melanin coated article comprising the steps of:
  applying a composition comprising melanin to the surface of an article; and
  drying the composition.

Clause 17. The method of clause 16, wherein the drying step is after the step of applying the composition to the surface.

Clause 18. The method of clause 16 or clause 17, further comprising mixing the composition with an adherent.

Clause 19. The method of clause 18, wherein the adherent is a polymer.

Clause 20. The method of any one of clauses 16-19, wherein the composition comprising melanin comprises melanin producing microbes, bioflakes, purified cell wall-associated melanin, extracellular vesicles comprising melanin, microshells, or a combination thereof.

Clause 21. The method of any one of clauses 16-20, wherein the melanin comprises cell wall-associated melanin produced using the method of any one of clauses 1-10.

Clause 22. The method of any one of clauses 16-21, wherein the melanin comprises extracellular melanin nanoparticles produced using the method of any one of clauses 11-14.

Clause 23. The method of clause 20, wherein the melanin producing microbe is selected from the group consisting of *Cryptococcus neoformans*, *Aureobasidium melanogenum*, *Exophiala dermititidis*, *Cryomyces antarcticus* and *Cryptococcus* chs3, *Cryptococcus* csr2, *Cryptococcus* pgi1, modified cell wall mutants thereof, *Agaricus biscporus*, *Cladosporium sphaerospermum*, and combinations thereof.

Clause 24. The method of any one of clauses 16-23, wherein the surface of the article is selected from the group consisting of plastic, glass, metal, wood, ceramic, aluminum, fibers, and polystyrene.

Clause 25. A melanin coated article, comprising:
an article; and
a coating supported by the surface of the article, wherein the coating comprises a composition comprising melanin to the surface of an article.

Clause 26. The article of clause 25, wherein the composition comprising melanin comprises melanin producing microbes, bioflakes, purified cell wall-associated melanin, extracellular vesicles comprising melanin, microshells or a combination thereof.

Clause 27. The article of clauses 25 or 26, wherein the melanin comprises cell wall-associated melanin produced using the method of any one of clauses 1-10.

Clause 28. The article of any of clauses 25-27, wherein the melanin comprises extracellular melanin nanoparticles produced using the method of any one of clauses 11-14.

Clause 29. The method of clause 26, wherein the melanin producing microbe is selected from the group consisting of *Cryptococcus neoformans*, *Aureobasidium melanogenum*, *Exophiala dermititidis*, *Cryomyces antarcticus* and *Cryptococcus* chs3, *Cryptococcus* csr2, *Cryptococcus* pgi1, modified cell wall mutants thereof, *Agaricus biscporus*, *Cladosporium sphaerospermum*, and combinations thereof.

Clause 30. The article of any of clauses 25-29, wherein the coating covers at least a portion of the surface of the article.

Clause 31. The article of any of clauses 25-30, wherein the surface of the article comprises plastic, glass, metal, wood, ceramic, aluminum, polystyrene, fibers, or a combination thereof.

Clause 32. A method of heating an article comprising the steps of:
providing the article of clause 25; and
exposing the article to light,
whereby the temperature of the article is increased.

Clause 33. The method of clause 32, wherein the light is ultraviolet light, infrared light, visible light, or a combination thereof.

Clause 34. The method of clause 32 or clause 33, further comprising contacting the article to a material, wherein the material increases in temperature.

What is claimed is:

1. A method of purifying cell wall-associated melanin comprising the steps of:
heating a melanin producing microbe in 6N hydrochloric acid (HCl); and
extracting the melanin using a chloroform:methanol:saline mixture.

2. The method of claim 1, wherein the heating steps are performed before the extracting step.

3. The method of claim 1, wherein the heating step has a temperature in the range of 60° C. to 120° C.

4. The method of claim 1, wherein the heating step has a duration in the range of 30 minutes to 24 hours.

5. The method of claim 1, wherein the heating step has a duration of 30 minutes to 3 hours.

6. The method of claim 1, wherein the chloroform:methanol:saline mixture has a concentration of about 8 parts chloroform, about 4 parts methanol, and about 3 parts saline.

7. The method of claim 1, further comprising repeating the extracting step at least once.

8. The method of claim 7, wherein the extracting step is repeated twice.

9. The method of claim 1, wherein the melanin producing microbe is a melanotic fungi.

10. The method of claim 1, wherein the melanin producing microbe is selected from the group consisting of *Cryptococcus neoformans*, *Aureobasidium melanogenum*, *Exophiala dermititidis*, *Cryomyces antarcticus* and *Cryptococcus* chs3, *Cryptococcus* csr2, *Cryptococcus* pgi1, modified cell wall mutants thereof, *Agaricus biscporus*, *Cladosporium sphaerospermum*, and combinations thereof.

* * * * *